United States Patent
Uchiyama et al.

(10) Patent No.: US 8,260,398 B2
(45) Date of Patent: Sep. 4, 2012

(54) POSITION DETECTION SYSTEM, MEDICAL-DEVICE GUIDANCE SYSTEM, AND POSITION DETECTION METHOD

(75) Inventors: Akio Uchiyama, Tokyo (JP); Ryoji Sato, Tokyo (JP); Atsushi Kimura, Tokyo (JP)

(73) Assignee: Olympus Corporation, Tokyo (JP)

( * ) Notice: Subject to any disclaimer, the term of this patent is extended or adjusted under 35 U.S.C. 154(b) by 618 days.

(21) Appl. No.: 12/443,605

(22) PCT Filed: Nov. 27, 2007

(86) PCT No.: PCT/JP2007/072849
§ 371 (c)(1),
(2), (4) Date: Mar. 30, 2009

(87) PCT Pub. No.: WO2008/066036
PCT Pub. Date: Jun. 5, 2008

(65) Prior Publication Data
US 2010/0073185 A1    Mar. 25, 2010

(30) Foreign Application Priority Data
Nov. 27, 2006 (JP) ................................. 2006-319095

(51) Int. Cl.
*A61B 5/05* (2006.01)
(52) U.S. Cl. ........................ 600/424; 600/407; 340/686.1
(58) Field of Classification Search .................... None
See application file for complete search history.

(56) References Cited

U.S. PATENT DOCUMENTS
| | | |
|---|---|---|
| 6,511,417 B1 | 1/2003 | Taniguchi et al. |
| 2003/0055317 A1 | 3/2003 | Taniguchi et al. |
| 2004/0124105 A1 | 7/2004 | Seiler et al. |
| 2005/0216231 A1* | 9/2005 | Aoki et al. ................... 702/183 |
| 2006/0125472 A1 | 6/2006 | Howard et al. |

FOREIGN PATENT DOCUMENTS
| | | |
|---|---|---|
| JP | 2000-081303 | 3/2000 |
| JP | 2005-121573 | 5/2005 |
| JP | 2006-177684 | 7/2006 |
| WO | 2005/120345 A2 | 12/2005 |

OTHER PUBLICATIONS

Extended Supplementary European Search Report dated Jul. 6, 2011.
Tokunaga Y. et al., "Precision Position-Detecting System Using an LC Resonant Magnetic Marker", Journal of the Magnetics Society of Japan (2005), vol. 29, No. 2, pp. 153-156.

* cited by examiner

*Primary Examiner* — Long V. Le
*Assistant Examiner* — Nicholas Evoy
(74) *Attorney, Agent, or Firm* — Scully, Scott, Murphy & Presser, P.C.

(57) ABSTRACT

There is provided a position detection system (1) including a first marker (4) that produces a first alternating magnetic field having a first position-calculating frequency by means of an external power supply; a second marker (3) including a magnetic induction coil (5) having a resonance frequency equal to the position-calculating frequency; a magnetic-field detection section (13) that is disposed outside a working region of the second marker (3) and that detects a magnetic field at the first position-calculating frequency; an extracting section (24) that extracts, from the detected magnetic field, a first detection-magnetic-field component having the first position-calculating frequency and having the same phase as the phase of the first alternating magnetic field; and a position/orientation analyzing section (22) that calculates at least one of the position and the orientation of the first marker (4) based on the intensity of the extracted first detection-magnetic-field component.

12 Claims, 24 Drawing Sheets

US 8,260,398 B2

POSITION DETECTION SYSTEM, MEDICAL-DEVICE GUIDANCE SYSTEM, AND POSITION DETECTION METHOD

TECHNICAL FIELD

The present invention relates to a position detection system, a medical-device guidance system, and a position detection method.

BACKGROUND ART

Position detection apparatuses that detect the position of a marker inserted into a body cavity by causing the marker to produce an alternating magnetic field by means of external power supply and then detecting, outside the body, the alternating magnetic field produced by the marker are well known (e.g., refer to Patent Document 1).

Position detection systems for capsule medical devices that detect the position and the orientation of a capsule medical device delivered into the body of a subject by externally producing a position-detecting magnetic field and detecting the absolute-value intensity of an induced magnetic field produced in a magnetic induction coil disposed in the capsule medical device are also well known (e.g., refer to Non-patent Document 1).

Patent Document 1:
Japanese Unexamined Patent Application, Publication No. 2000-81303

Non-patent Document 1:
Tokunaga plus 7 other authors. Precision Position-detecting System Using an LC Resonant Magnetic Marker. Journal of the Magnetics Society of Japan 2005; Vol. 29, No. 2:153-156

DISCLOSURE OF INVENTION

However, if a first marker which produces an alternating magnetic field by external power supply coexists with a second marker which includes a resonance circuit having a resonance frequency in the proximity of the frequency of that alternating magnetic field, then an induced magnetic field is produced from the resonance circuit of the second marker due to the alternating magnetic field produced by the first marker. As a result, because merely detecting the absolute-value intensity of the magnetic field at the frequency of the alternating magnetic field involves simultaneous detection of the induced magnetic field, the magnetic-field intensity obtained in this case differs from the magnetic-field intensity obtained in a case where the alternating magnetic field alone is detected. For this reason, it has been difficult to accurately calculate the position or the orientation of the first marker.

An object of the present invention is to provide a position detection system, a medical-device guidance system, and a position detection method capable of accurately detecting the position or the orientation of a first marker which produces an alternating magnetic field by means of external power supply even though the first marker coexists with a second marker which includes a resonance circuit having a resonance frequency the same as or close to the frequency of the alternating magnetic field.

To achieve the above-described object, the present invention provides the following solutions.

A position detection system according to a first aspect of the present invention includes a first marker that produces a first alternating magnetic field having a first position-calculating frequency by means of an external power supply; a second marker including a magnetic induction coil having a resonance frequency equal to the position-calculating frequency; a magnetic-field detection section that is disposed outside a working region of the second marker and that detects a magnetic field at the first position-calculating frequency; an extracting section that extracts, from the magnetic field detected by the magnetic-field detection section, a first detection-magnetic-field component having the first position-calculating frequency and having a phase equal to a phase of the first alternating magnetic field; and a position/orientation analyzing section that calculates at least one of a position and an orientation of the first marker based on the intensity of the first detection-magnetic-field component extracted by the extracting section.

According to the first aspect of the present invention, the first marker produces the first alternating magnetic field having the first position-calculating frequency using the external power supply. The magnetic induction coil mounted in the second marker receives the first alternating magnetic field produced from the first marker. Because the resonance frequency of a circuit including the magnetic induction coil is equal to the first position-calculating frequency, the magnetic induction coil produces an induced magnetic field in response to the first alternating magnetic field. Then, the magnetic-field detection section detects the magnetic field including the first alternating magnetic field and the induced magnetic field at the first position-calculating frequency.

The extracting section extracts, from the magnetic field detected by the magnetic-field detection section, the first detection-magnetic-field component having the first position-calculating frequency and having the same phase as that of the first alternating magnetic field. The position/orientation analyzing section calculates at least one of the position and the orientation of the first marker based on the intensity of the first detection-magnetic-field component extracted by the extracting section.

The induced magnetic field produced from the magnetic induction coil in response to the first alternating magnetic field has the first position-calculating frequency and a phase shifted by $\pi/2$ relative to the phase of the first alternating magnetic field. On the other hand, the first detection-magnetic-field component is a magnetic-field component having the same frequency and phase as those of the first alternating magnetic field.

For this reason, of the detected magnetic field, the first detection-magnetic-field component does not include information about the induced magnetic field but includes only information about the first alternating magnetic field. Therefore, the extracting section can extract only information about the first alternating magnetic field from the magnetic field detected by the magnetic-field detection section. Because of this, the position/orientation analyzing section can calculate at least one of the position and the orientation of the first marker using only the information about the intensity associated with the first alternating magnetic field produced from the first marker.

Consequently, even though the first marker that produces a magnetic field using the external power supply coexists with the second marker having the magnetic induction coil, the position or the orientation of the first marker can be calculated with high accuracy without being affected by the induced magnetic field.

In the above-described first aspect, the extracting section may extract, from the magnetic field detected by the magnetic-field detection section, a second detection-magnetic-field component having the first position-calculating frequency and having a phase shifted by $\pi/2$ with respect to the phase of the first alternating magnetic field, and the position/orientation analyzing section may calculate at least one of a position and an orientation of the second marker based on the intensity of the second detection-magnetic-field component.

By doing so, the extracting section extracts the first detection-magnetic-field component and the second detection-magnetic-field component from the magnetic field detected by the magnetic-field detection section. The position/orientation analyzing section calculates at least one of the position and the orientation of the first marker based on the intensity of the first detection-magnetic-field component extracted by the extracting section, and calculates at least one of the position and the orientation of the second marker based on the intensity of the second detection-magnetic-field component extracted by the extracting section.

The induced magnetic field produced from the magnetic induction coil in response to the first alternating magnetic field has the same frequency as that of the first alternating magnetic field and a phase shifted by $\pi/2$ relative to the phase of the first alternating magnetic field. The second detection-magnetic-field component is also a magnetic-field component having the same frequency as that of the first alternating magnetic field and a phase shifted by $\pi/2$ relative to the phase of the first alternating magnetic field. For this reason, the second detection-magnetic-field component does not include information about the first alternating magnetic field but includes only information about the induced magnetic field. Therefore, the extracting section can extract only information about the induced magnetic field from the magnetic field detected by the magnetic-field detection section.

Because of this, the position/orientation analyzing section can calculate at least one of the position and the orientation of the second marker using only the intensity information of the induced magnetic field produced from the second marker.

Consequently, even though the first marker that produces a magnetic field using the external power supply coexists with the second marker having the magnetic induction coil, at least one of the position and the orientation can be simultaneously calculated with high accuracy for both the first marker and the second marker.

Furthermore, the position detection system according to the above-described first aspect may include a magnetic-field generating unit, disposed outside a working region of the second marker, that produces a second alternating magnetic field having the first position-calculating frequency and having a phase equal to the phase of the first alternating magnetic field. The position/orientation analyzing section may calculate at least one of the position and the orientation of the first marker based on a difference between an intensity of the first detection-magnetic-field component extracted when the first alternating magnetic field is produced and an intensity of the first detection-magnetic-field component extracted before the first alternating magnetic field is produced.

By doing so, the magnetic-field generating unit disposed outside the working region of the second marker produces the second alternating magnetic field. Because the first alternating magnetic field and the second alternating magnetic field have the same frequency and phase, the magnetic induction coil produces the induced magnetic field in response to the first alternating magnetic field and the second alternating magnetic field. The magnetic-field detection section detects a magnetic field including the first alternating magnetic field, the second alternating magnetic field, and the induced magnetic field at the first position-calculating frequency.

The first detection-magnetic-field component when the first alternating magnetic field is produced includes information about the first alternating magnetic field and the second alternating magnetic field. On the other hand, the first detection-magnetic-field component extracted before the first alternating magnetic field is produced includes only information about the second alternating magnetic field. Therefore, only the information about the intensity of the first alternating magnetic field can be obtained by calculating the difference between them through an operation performed by the position/orientation analyzing section.

For the same reason as described above, the second detection-magnetic-field component does not include information about the first alternating magnetic field and the second alternating magnetic field but includes only information about the induced magnetic field. Therefore, the extracting section can extract only the information about the induced magnetic field from the magnetic field detected by the magnetic-field detection section. Because of this, the position/orientation analyzing section can calculate at least one of the position and the orientation of the first marker using only information about the intensity of the first alternating magnetic field and can calculate at least one of the position and the orientation of the second marker using only intensity information of the induced magnetic field produced from the second marker.

Consequently, even though the first marker that produces a magnetic field using the external power supply coexists with the second marker having the magnetic induction coil, at least one of the position and the orientation can be simultaneously calculated with high accuracy for both the first marker and the second marker. Furthermore, because the second alternating magnetic field, in addition to the first alternating magnetic field, causes the second marker to produce the induced magnetic field, the intensity of the induced magnetic field can be increased.

Furthermore, the position detection system according to the above-described first aspect may include a magnetic-field generating unit, disposed outside a working region of the second marker, that produces a second alternating magnetic field having at least one set of second position-calculating frequencies that are in the proximity of the first position-calculating frequency and are separated by a predetermined frequency with respect to the first position-calculating frequency with the first position-calculating frequency interposed therebetween. The magnetic-field detection section may detect a magnetic field at the second position-calculating frequency, the extracting section may extract, from the magnetic field detected by the magnetic-field detection section, a difference between intensities of at least one set of second detection-magnetic-field components having the one set of second position-calculating frequencies, and the position/orientation analyzing section may calculate at least one of a position and an orientation of the second marker based on the extracted difference.

The magnetic-field generating unit disposed outside the working region of the second marker produces the second alternating magnetic field. The magnetic induction coil produces the induced magnetic field having the first position-calculating frequency in response to the first alternating magnetic field and produces the induced magnetic field having the second position-calculating frequency in response to the second alternating magnetic field. The magnetic-field detection section detects a magnetic field including the first alternating magnetic field and the induced magnetic field produced by the first alternating magnetic field at the first position-calculating frequency and detects a magnetic field including the second alternating magnetic field and the induced magnetic field produced by the second alternating magnetic field at the second position-calculating frequency.

The extracting section extracts the difference between the intensity of the first detection-magnetic-field component and the intensities of at least one set of second detection-magnetic-field components from the magnetic field detected by the magnetic-field detection section. The position/orientation analyzing section calculates at least one of the position and the orientation of the first marker based on the intensity of the first detection-magnetic-field component extracted by the extracting section and furthermore, calculates at least one of the position and the orientation of the second marker based on the difference between the intensities of the extracted at least one set of second detection-magnetic-field components.

The induced magnetic field produced from the magnetic induction coil in response to the second alternating magnetic field has a set of second position-calculating frequencies, and the intensities with respect to the second alternating magnetic field differ from one another at the frequencies. On the other hand, because the second detection-magnetic-field component is a magnetic-field component having the second position-calculating frequency, it has the same frequency as that of the second alternating magnetic field.

For this reason, the second detection-magnetic-field component does not include information about the first alternating magnetic field but includes only information about the second alternating magnetic field and the induced magnetic field produced by the second alternating magnetic field (hereinafter, referred to as the induced magnetic field associated with the second alternating magnetic field). Therefore, through arithmetic calculation of the difference between the intensities of a set of second detection-magnetic-field components, the extracting section can extract a large amount of information about the intensity of the induced magnetic field associated with the second alternating magnetic field by subtracting the information about the intensity of the second alternating magnetic field from the magnetic field detected by the magnetic-field detection section.

Because of this, the position/orientation analyzing section can calculate at least one of the position and the orientation of the second marker using the information about the intensity of the induced magnetic field associated with the second alternating magnetic field. Consequently, even though the first marker that produces a magnetic field using the external power supply coexists with the second marker having the magnetic induction coil, at least one of the position and the orientation can be simultaneously calculated with high accuracy for both the first marker and the second marker.

In addition, in the above-described first aspect, the intensities of the second detection-magnetic-field components may be absolute-value intensities.

The absolute-value intensity of the second detection-magnetic-field component includes only information about the second alternating magnetic field and the induced magnetic field associated with the second alternating magnetic field. Therefore, through arithmetic operation of the difference between the intensities of a set of second detection-magnetic-field components, the extracting section can extract a large amount of information about the intensity of the induced magnetic field associated with the second alternating magnetic field by subtracting the information about the intensity of the second alternating magnetic field from the magnetic field detected by the magnetic-field detection section.

In addition, in the above-described first aspect, the second marker may be provided in a capsule medical device.

Furthermore, in the above-described first aspect of the invention, the first marker may be provided at a front end portion of an endoscope.

A medical-device guidance system according to a second aspect of the present invention includes one of the above-described position detection systems, the second marker further including a magnetic-field acting section; a propulsion-magnetic-field generating unit that produces a propulsion magnetic field made to act upon the magnetic-field acting section; and a propulsion-magnetic-field control section that controls an intensity and a direction of the propulsion magnetic field based on at least one of the position and the orientation of the second marker calculated by the position/orientation analyzing section.

According to the second aspect of the present invention, the propulsion-magnetic-field generating unit produces the propulsion magnetic field which is made to act upon the magnetic-field acting section of the second marker. The propulsion-magnetic-field control section controls the propulsion-magnetic-field generating unit based on at least one of the position and the orientation of the second marker calculated by the position/orientation analyzing section and controls the intensity and the direction of the propulsion magnetic field. Consequently, propulsion of the second marker can be controlled based on the position or the orientation of the second marker.

A position detection method according to a third aspect of the present invention includes a magnetic-field generating step of causing a first marker to produce a first alternating magnetic field having a first position-calculating frequency by means of an external power supply; an induced-magnetic-field generating step of causing a second marker including a magnetic induction coil to produce an induced magnetic field in response to the first alternating magnetic field; a magnetic-field detecting step of detecting a magnetic field at the first position-calculating frequency; an extracting step of extracting, from the detected magnetic field, a first detection-magnetic-field component having the first position-calculating frequency and having a phase equal to a phase of the first alternating magnetic field at the first position-calculating frequency; and a position/orientation analyzing step of calculating at least one of a position and an orientation of the first marker based on the intensity of the extracted first detection-magnetic-field component.

In the above-described third aspect, the extracting step may include a step of extracting, from the detected magnetic field, a second detection-magnetic-field component having the first position-calculating frequency and having a phase shifted by $\pi/2$ with respect to the phase of the first alternating magnetic field, and the position/orientation analyzing step may include a step of calculating at least one of a position and an orientation of the second marker based on the intensity of the extracted second detection-magnetic-field component.

Furthermore, in the above-described third aspect, the magnetic-field generating step may include a step of producing a second alternating magnetic field having the first position-calculating frequency and having a phase equal to the phase of the first alternating magnetic field, the induced-magnetic-field generating step may include a step of causing the second marker to produce an induced magnetic field in response to the second alternating magnetic field, and the position/orientation analyzing step may include a step of calculating at least one of the position and the orientation of the first marker based on a difference between an intensity of the first detection-magnetic-field component extracted when the first alternating magnetic field is produced and an intensity of the first detection-magnetic-field component extracted before the first alternating magnetic field is produced.

In addition, in the above-described third aspect, the magnetic-field generating step may include a step of producing a second alternating magnetic field having at least one set of second position-calculating frequencies that are in the proximity of the first position-calculating frequency and are separated by a predetermined frequency with respect to the first position-calculating frequency with the first position-calculating frequency interposed therebetween, the induced-magnetic-field generating step may include a step of causing the second marker to produce an induced magnetic field in response to the second alternating magnetic field, the magnetic-field detecting step may include a step of detecting a magnetic field at the second position-calculating frequency, the extracting step may include a step of extracting, from a detected magnetic field, a difference between intensities of at least one set of second detection-magnetic-field components having the one set of second position-calculating frequencies, and the position/orientation analyzing step may include a step of calculating at least one of a position and an orientation of the second marker based on the extracted difference.

The present invention affords an advantage in that, even though a first marker that produces an alternating magnetic field using an external power supply coexists with a second marker including a resonance circuit having a resonance frequency equal or close to the frequency of the alternating magnetic field, the position or the orientation of the first marker can be detected accurately.

Figure 1:
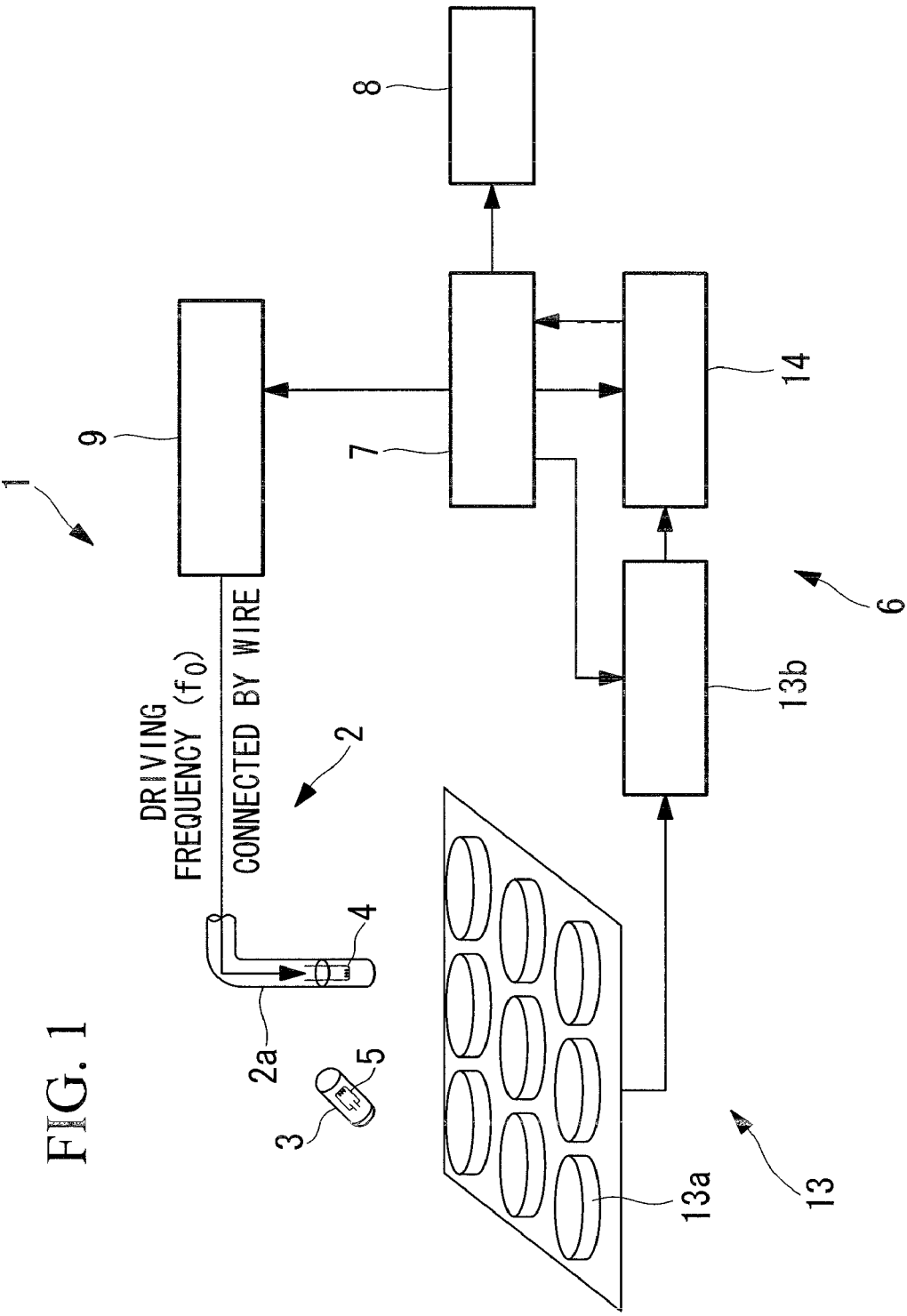
FIG. 1 is a block diagram depicting the overall structure of a position detection system according to a first embodiment of the present invention.

EXPLANATION OF REFERENCE SIGNS $f_0$: First position-calculating frequency
$f_1$, $f_2$: Second position-calculating frequency
1, 40, 50: Position detection system
2: Endoscope apparatus (endoscope)
2a: Inserting section
3: Capsule medical device (second marker)
3': Second capsule medical device (capsule medical device)
4, 52: Marker coil (first marker)
5: Magnetic induction coil
6: Magnetic-field detection section
21: Frequency-selecting section (extracting section)
22: Position/orientation analyzing section
41: Magnetic-field generating device (magnetic-field generating unit)
51: First capsule medical device (capsule medical device)
71: Three-axis Helmholtz coil unit
72: Helmholtz-coil driver (propulsion-magnetic-field control section)
100: Medical-device guidance system
150: Permanent magnet (magnetic-field acting section)

BEST MODE FOR CARRYING OUT THE INVENTION

First Embodiment

A position detection system 1 according to a first embodiment of the present invention will now be described with reference to FIGS. 1 to 3.

The position detection system 1 according to this embodiment is a system provided in a medical-device guidance system that includes an endoscope apparatus 2 having an inserting section 2a inserted into a body cavity and a capsule medical device 3 delivered into the body cavity. The position detection system 1 includes a marker coil (first marker) 4 disposed at a tip portion of the inserting section 2a of the endoscope apparatus 2, a magnetic induction coil (second marker) 5 disposed in the capsule medical device 3, a position detection apparatus 6 that detects the position of the marker coil 4, a control section 7 that controls these components, and a display device 8 that displays a result of detection by the position detection apparatus 6.

Figure 2:
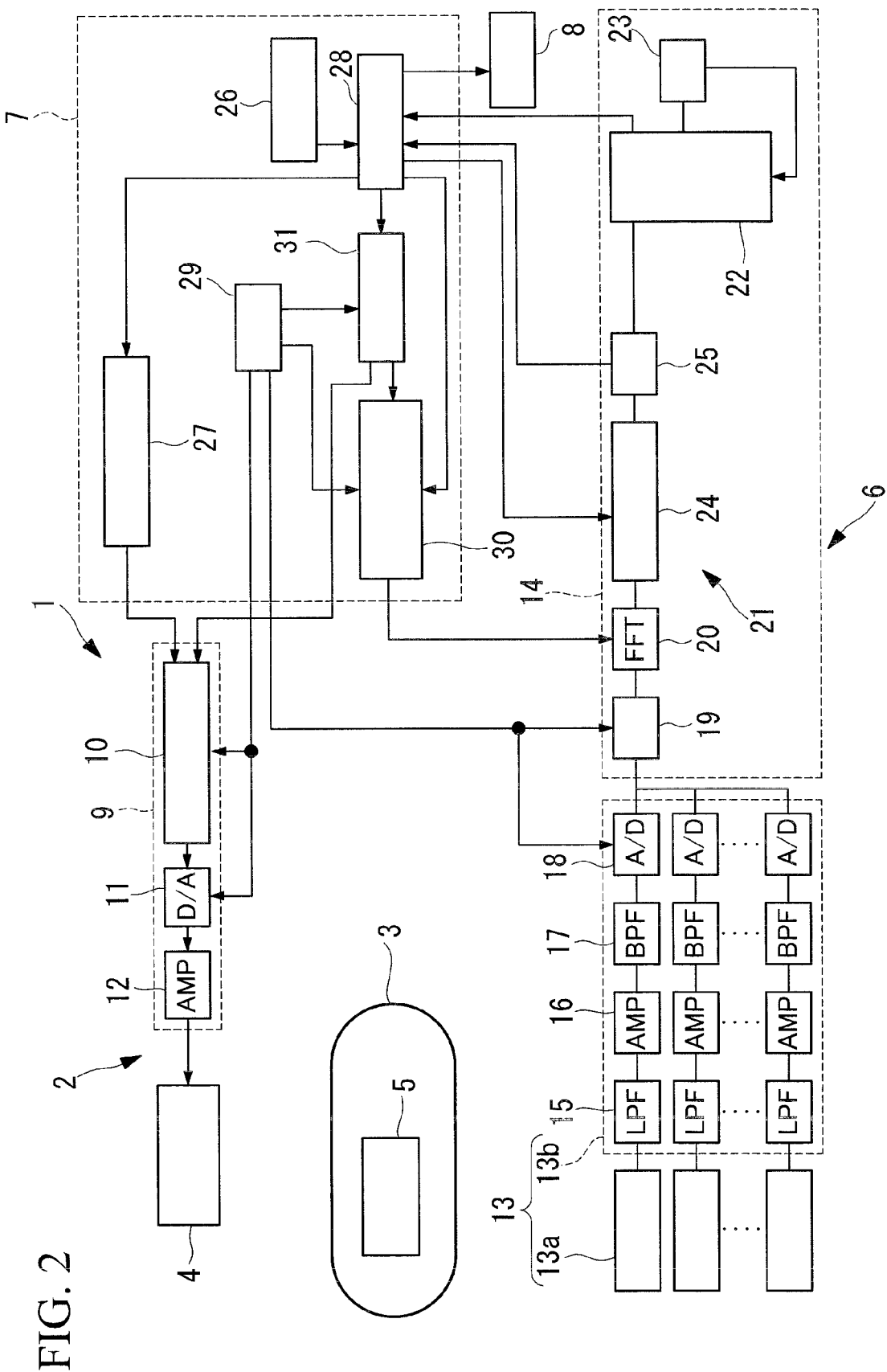
FIG. 2 is a block diagram depicting the detailed structure of the position detection system shown in FIG. 1.

As shown in FIG. 2, the endoscope apparatus 2 is provided with a marker-driving circuit 9 that causes the marker coil 4 to produce a first alternating magnetic field in response to a command signal from the control section 7. The marker-driving circuit 9 includes a waveform data memory 10 that stores a magnetic-field waveform of the first alternating magnetic field produced by the marker coil 4, a D/A converter 11, and an amplifier 12.

The above-described marker coil 4 is driven by the marker-driving circuit 9 to produce the first alternating magnetic field having a first position-calculating frequency $f_0$.

The capsule medical device 3 is provided with a resonance circuit that includes the above-described magnetic induction coil 5 and that has a resonance frequency equal to the first position-calculating frequency $f_0$. The magnetic induction coil 5 produces an induced magnetic field in response to an alternating magnetic field from outside.

The above-described position detection apparatus 6 is disposed outside the body of a subject into which the endoscope apparatus 2 and the capsule medical device 3 are inserted. The position detection apparatus 6 includes a magnetic-field detection section 13 that detects magnetic fields produced from the marker coil 4 and the magnetic induction coil 5 and a position-calculating section 14 that calculates the positions and the orientations of the endoscope apparatus 2 and the capsule medical device 3 based on the magnetic fields detected by the magnetic-field detection section 13.

The above-described magnetic-field detection section 13 includes a plurality of sense coils 13a and a receiving circuit 13b that receives an output signal from each of the sense coils 13a.

The sense coils 13a are each an air-core coil and are arranged in a square composed of one set of nine coils so as to face a working space of the tip of the inserting section 2a of the endoscope apparatus 2 and the capsule medical device 3.

The receiving circuit 13b includes low-pass filters (LPFs) 15 that remove high-frequency components of AC voltages having information about the position of the endoscope apparatus 2, amplifiers (AMPs) 16 that amplify the AC voltages from which high-frequency components have been removed, band-pass filters (BPFs) 17 that transmit only predetermined frequency ranges of the amplified AC voltages, and A/D converters 18 that convert the AC voltages that have passed through the band-pass filters 17 into digital signals. As a result, the magnetic fields detected in the magnetic-field detection section 13 are output as magnetic-field signals composed of digital signals.

The above-described position-calculating section 14 includes a first memory 19 that stores the magnetic-field signals output from the receiving circuit 13b of the magnetic-field detection section 13, an FFT-processing circuit 20 that applies frequency analysis processing to the magnetic-field signals, an extracting section 21 that extracts predetermined magnetic-field information from a result of frequency analysis processing of the magnetic-field signals, a position/orientation analyzing section 22 that calculates the positions and the orientations of the endoscope apparatus 2 and the capsule medical device 3 based on the extracted magnetic-field information, and a second memory 23 that stores the calculated positions and orientations of the endoscope apparatus 2 and the capsule medical device 3.

The above-described extracting section 21 includes a frequency-selecting section 24 that receives from the control section 7 the first position-calculating frequency $f_0$, which is a frequency component of the signal produced by the marker-driving circuit 9, and that extracts magnetic-field information having the first position-calculating frequency $f_0$ from among the magnetic-field information obtained by frequency analysis of the magnetic-field signals, as well as a third memory 25 that stores the magnetic-field information at the first position-calculating frequency $f_0$ extracted by the frequency-selecting section 24.

The phrase "magnetic-field information at the first position-calculating frequency $f_0$" refers to the absolute value, the real part (first detection-magnetic-field component), and the imaginary part (second detection-magnetic-field component) of the magnetic field at the first position-calculating frequency $f_0$. The real part is a magnetic-field component that has the first position-calculating frequency $f_0$ and the same phase as that of the above-described first alternating magnetic field. The imaginary part is a magnetic-field component that has the first position-calculating frequency $f_0$ and has a phase shifted by $\pi/2$ relative to the phase of the first alternating magnetic field.

From the magnetic-field information stored in the third memory 25, the above-described position/orientation analyzing section 22 calculates the position and the orientation of the capsule medical device 3 based on the imaginary parts of the magnetic fields detected by all the sense coils 13a and calculates the position and the orientation of the tip of the endoscope apparatus 2 based on the real parts and calibration values of the magnetic fields detected by all the sense coils 13a.

The above-described control section 7 includes an input device 26 used for various input operations, a waveform-data generator 27 that calculates a magnetic-field waveform to be produced from the marker coil 4 based on the resonance frequency of the magnetic induction coil 5 input by the relevant input device 26, and a control circuit 28 that transfers the input resonance frequency to the waveform-data generator 27. The control section 7 further includes a clock 29 that produces a predetermined clock signal, a read-out-timing generator 30 that instructs the FFT-processing circuit 20 of the position-calculating section 14 on the read-out timing of the magnetic-field signals used for frequency analysis based on the clock signal, and a trigger generator 31 that produces a trigger signal based on the clock signal.

The control circuit 28 instructs the trigger generator 31 to produce a trigger signal for the read-out-timing generator 30 and the marker-driving circuit 9. In addition, the above-described waveform-data generator 27 transfers the generated magnetic-field waveform to the waveform data memory 10 of the marker-driving circuit 9.

A method for detecting the positions of the tip of the endoscope apparatus 2 and the capsule medical device 3 using the position detection system 1 according to this embodiment with the above-described structure will be described below.

In order to detect the positions and the orientations of the tip of the endoscope apparatus 2 and the capsule medical device 3 using the position detection system 1 according to this embodiment, the positions and the orientations of the marker coil 4 at the tip of the endoscope apparatus 2 and of the magnetic induction coil 5 in the capsule medical device 3 are detected.

First, the magnetic-field waveform is produced from the marker coil 4 and is stored in the waveform data memory 10 of the marker-driving circuit 9. Next, each of the sense coils 13a is subjected to calibration, a calibration value is acquired, and read-out timing is set. Then, based on the acquired calibration values and the set read-out timing, actual measurement for calculating the positions and the orientations of the marker coil 4 and the magnetic induction coil 5 is carried out.

Figure 3:
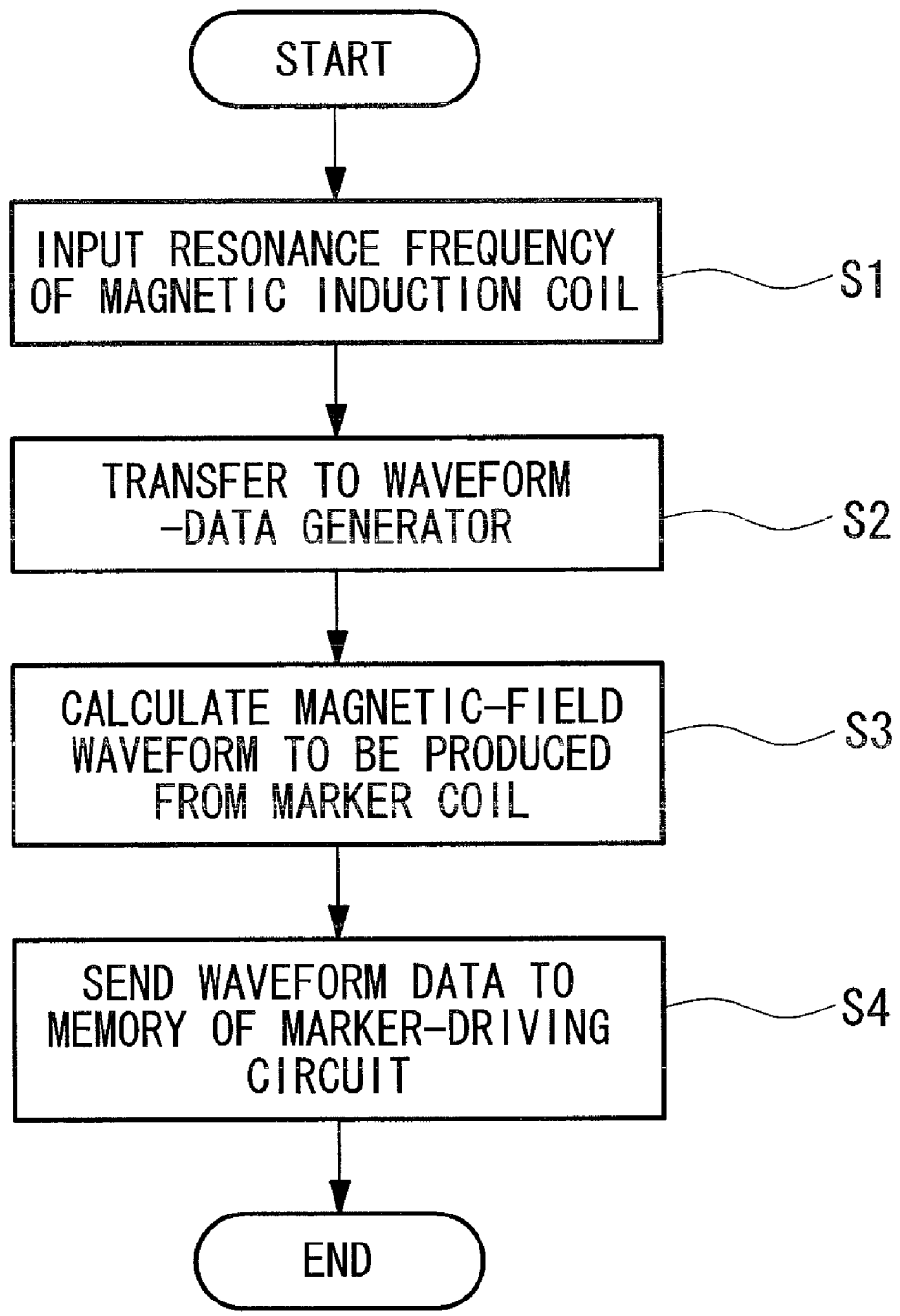
FIG. 3 is a flowchart illustrating waveform generation by a position detection method using the position detection system shown in FIG. 1.

As shown in FIG. 3, generation of a magnetic-field waveform is started by inputting the resonance frequency of the magnetic induction coil 5 from the input device 26 (step S1) and causing the control circuit 28 to transfer the input resonance frequency to the waveform-data generator 27 (step S2). In the waveform-data generator 27, the magnetic-field waveform produced from the marker coil 4 is calculated based on the sent resonance frequency of the magnetic induction coil 5 (step S3), and the calculated waveform data is stored in the waveform data memory 10 of the marker-driving circuit 9 (step S4).

Figure 4:
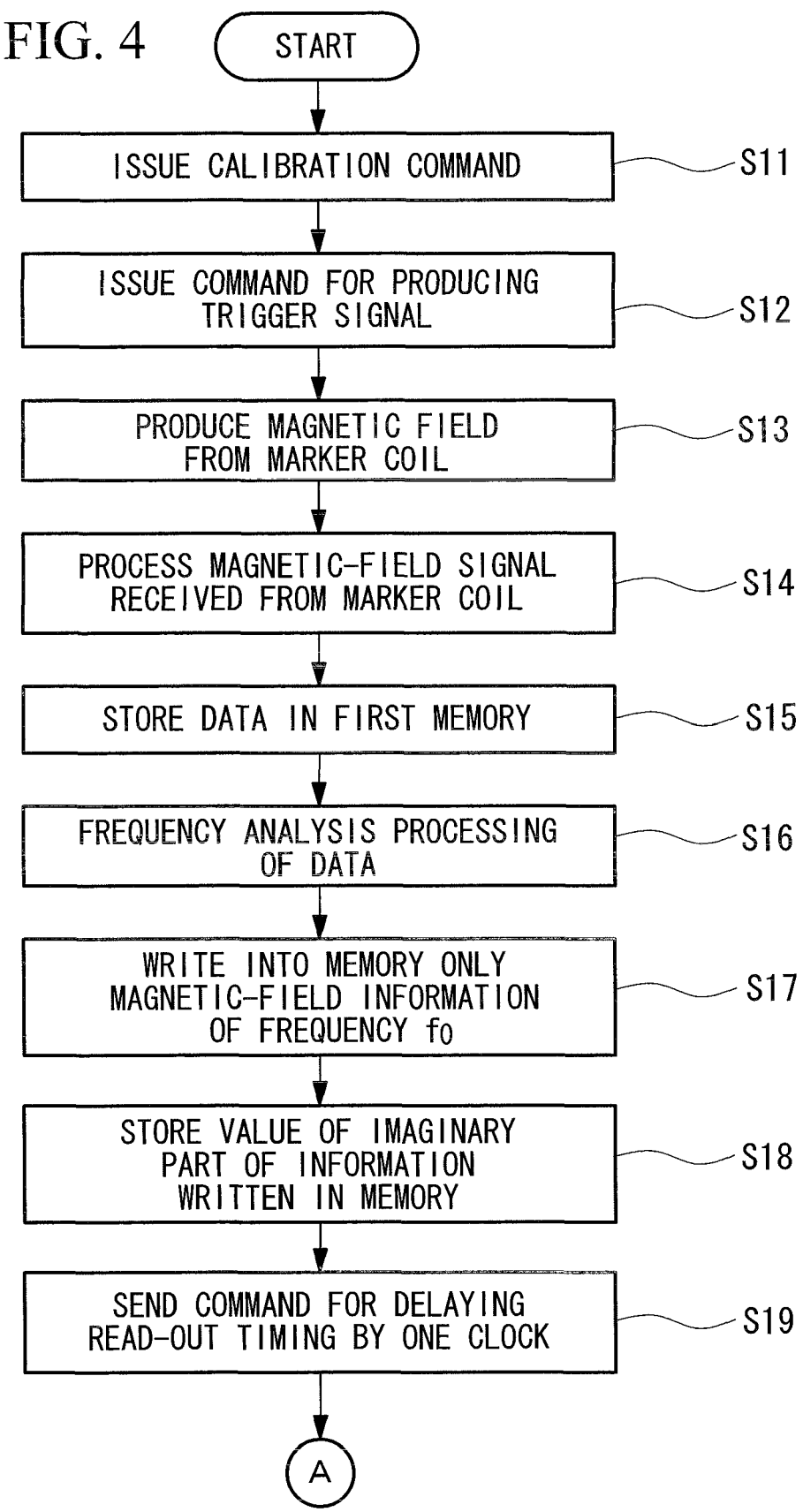
FIG. 4 is a flowchart illustrating the first-half stage of calibration in the position detection method of FIG. 3.
Figure 5:
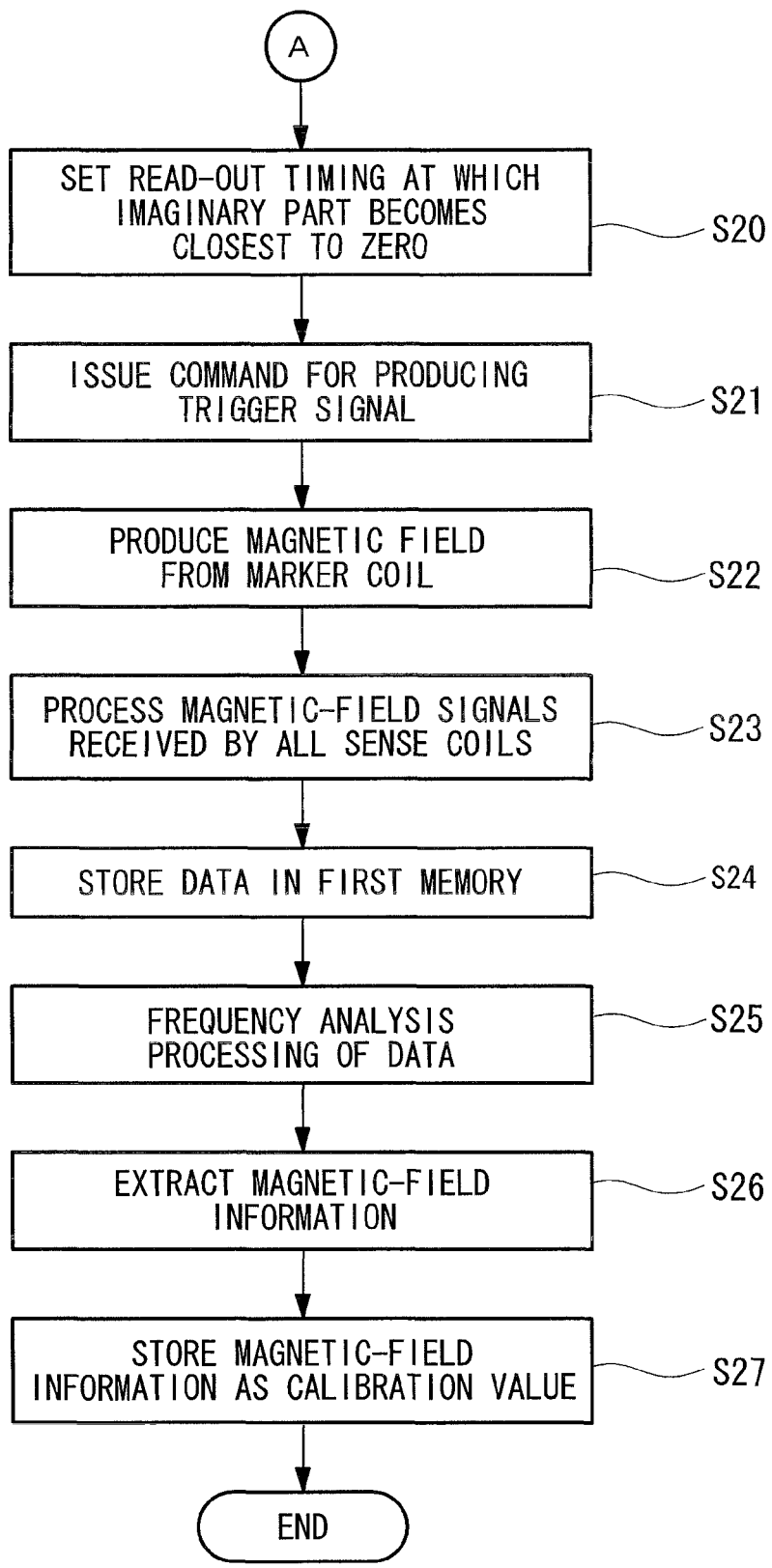
FIG. 5 is a flowchart illustrating the second-half stage of calibration in the position detection method of FIG. 3.

As shown in FIGS. 4 and 5, calibration is started when a calibration command is input from the input device 26 while the tip of the inserting section 2a of the endoscope apparatus 2 is in the body cavity and the capsule medical device 3 is not in the body cavity (step S11). The control circuit 28 instructs the trigger generator 31 to produce a trigger signal for the marker-driving circuit 9 and the read-out-timing generator 30. As a result, a trigger signal is issued from the trigger generator 31 (step S12).

The marker-driving circuit 9 that has received the trigger signal sequentially generates magnetic-field-generation driving signals in synchronization with the clock signal from the clock 29 based on the waveform data stored in the waveform data memory 10 and outputs them to the marker coil 4. The marker coil 4 produces the first alternating magnetic field based on the input magnetic-field-generation driving signals (step S13).

The receiving circuit 13b receives a magnetic-field signal associated with the first alternating magnetic field from the marker coil 4 detected by each of the sense coils 13a; performs low-pass filtering with a low-pass filter 15, amplification with an amplifier 16, and band-pass filtering with a band-pass filter 17; and then performs A/D conversion in synchronization with the clock signal (step S14).

The magnetic-field signal that has been subjected to A/D conversion is stored in the first memory 19 of the position-calculating section 14 (step S15). Thereafter, it is determined whether or not a number of items of data required to perform frequency analysis processing are accumulated in the first memory 19, and if the required number of items of data are accumulated, frequency analysis processing is performed by the FFT-processing circuit 20 (step S16).

Based on the result of frequency analysis processing, the frequency-selecting section 24 extracts only the magnetic-field information at the first position-calculating frequency $f_0$, which is the frequency of the first alternating magnetic field produced from the marker coil 4, and stores it in the third memory 25 (step S17).

The control circuit 28 reads out the magnetic-field information stored in the third memory 25 and stores the value of the imaginary part in an internal memory (not shown in the figure) (step S18).

Then, the control circuit 28 sends to the read-out-timing generator 30 a command for delaying by one clock the read-out timing to be generated in the read-out-timing generator 30 (step S19).

Thereafter, while repeating steps S12 to S19, the control circuit 28 compares the imaginary part of the magnetic-field information stored in the third memory 25 with the imaginary part stored in the internal memory. The control circuit 28 sets, in the read-out-timing generator 30, the read-out timing that causes the value of the imaginary part in the result of the frequency analysis processing stored at step S18 to become closest to zero as the read-out timing used for actual measurement (step S20).

Measurement of a calibration value is carried out while the read-out timing that causes the value of the imaginary part in the result of the frequency analysis processing to become closest to zero is set in the read-out-timing generator 30, as described above.

More specifically, the control circuit 28 instructs the trigger generator 31 to produce a trigger signal for the marker-driving circuit 9 and the read-out-timing generator 30 (step S21). Then, based on the waveform data stored in the waveform data memory 10, the marker-driving circuit 9 sequentially produces magnetic-field-generation driving signals in synchronization with the clock signal and outputs them to the marker coil 4. The marker coil 4 produces the first alternating magnetic field based on the input magnetic-field-generation driving signals (step S22).

Next, the receiving circuit 13b applies low-pass filtering, amplification, and band-pass filtering to the magnetic-field signals from the marker coil 4 received by all the sense coils 13a and performs A/D conversion in synchronization with the clock signal (step S23). The magnetic-field signals that have been subjected to A/D conversion are accumulated in the first memory 19 of the position-calculating section 14 (step S24).

Thereafter, the FFT-processing circuit 20 reads out the magnetic-field signals detected by all the sense coils 13a from the first memory 19 with the above-described read-out timing and performs frequency analysis processing (step S25). The frequency-selecting section 24 extracts the real part value, the imaginary part value, and the absolute value of the magnetic-field intensity at the first position-calculating frequency $f_0$ from the magnetic-field information obtained as a result of the frequency analysis processing (step S26) and stores the extracted values in the third memory 25 as calibration values corresponding to the respective sense coils 13a (step S27). This completes calibration processing, followed by actual measurement.

Figure 6:
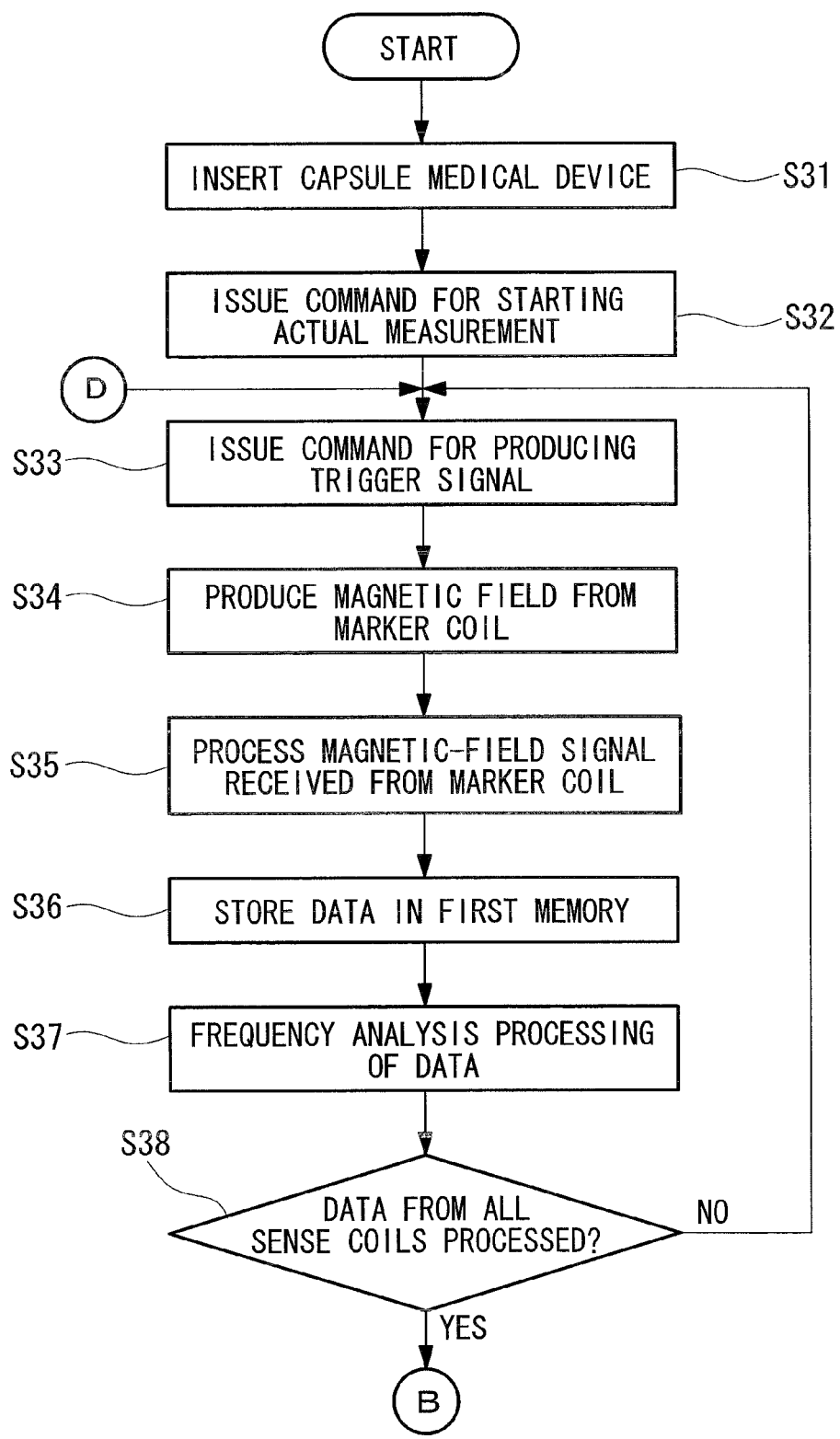
FIG. 6 is a flowchart illustrating the first-half stage of actual measurement in the position detection method of FIG. 3.
Figure 7:
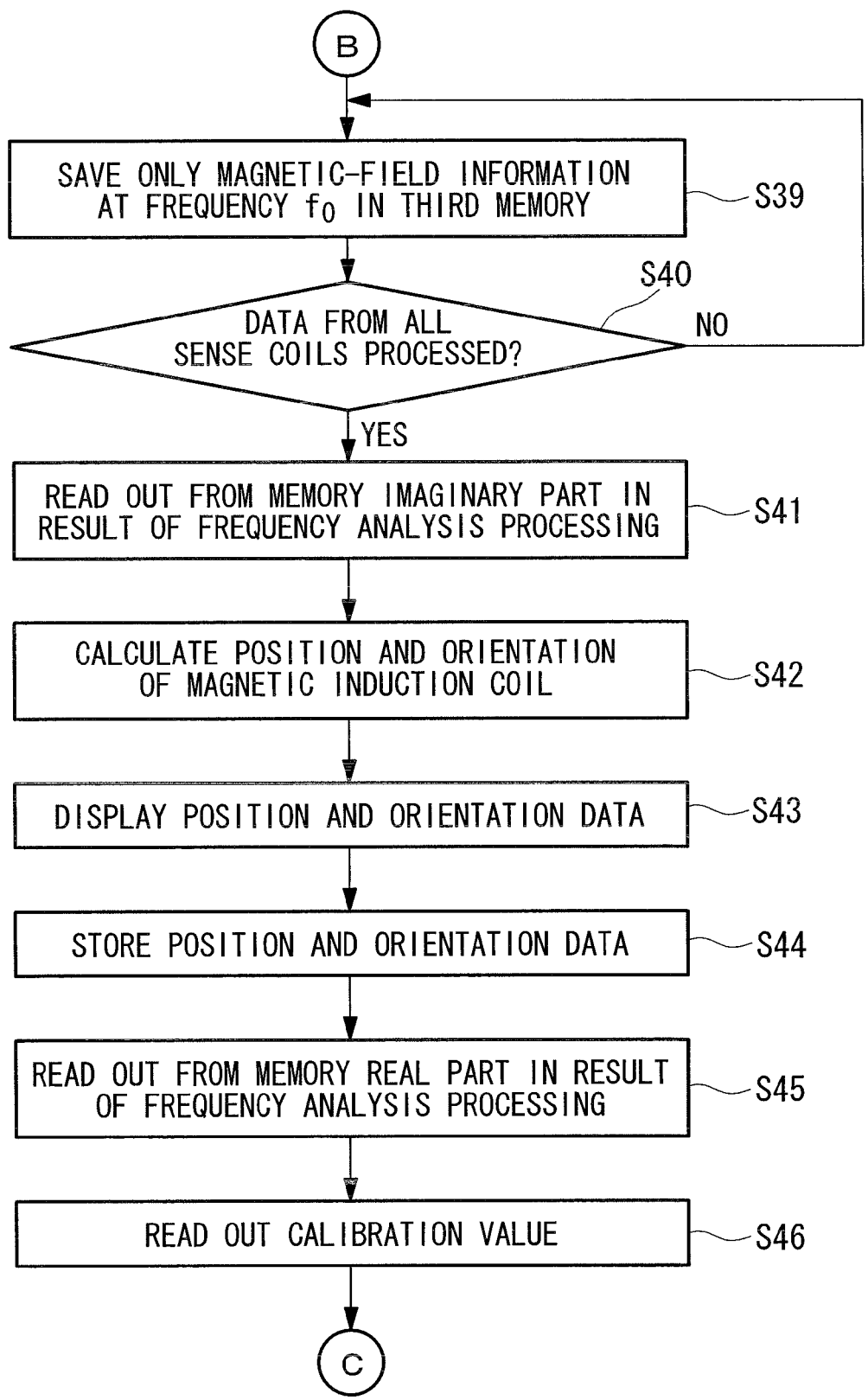
FIG. 7 is a flowchart illustrating actual measurement, continued from FIG. 6.
Figure 8:
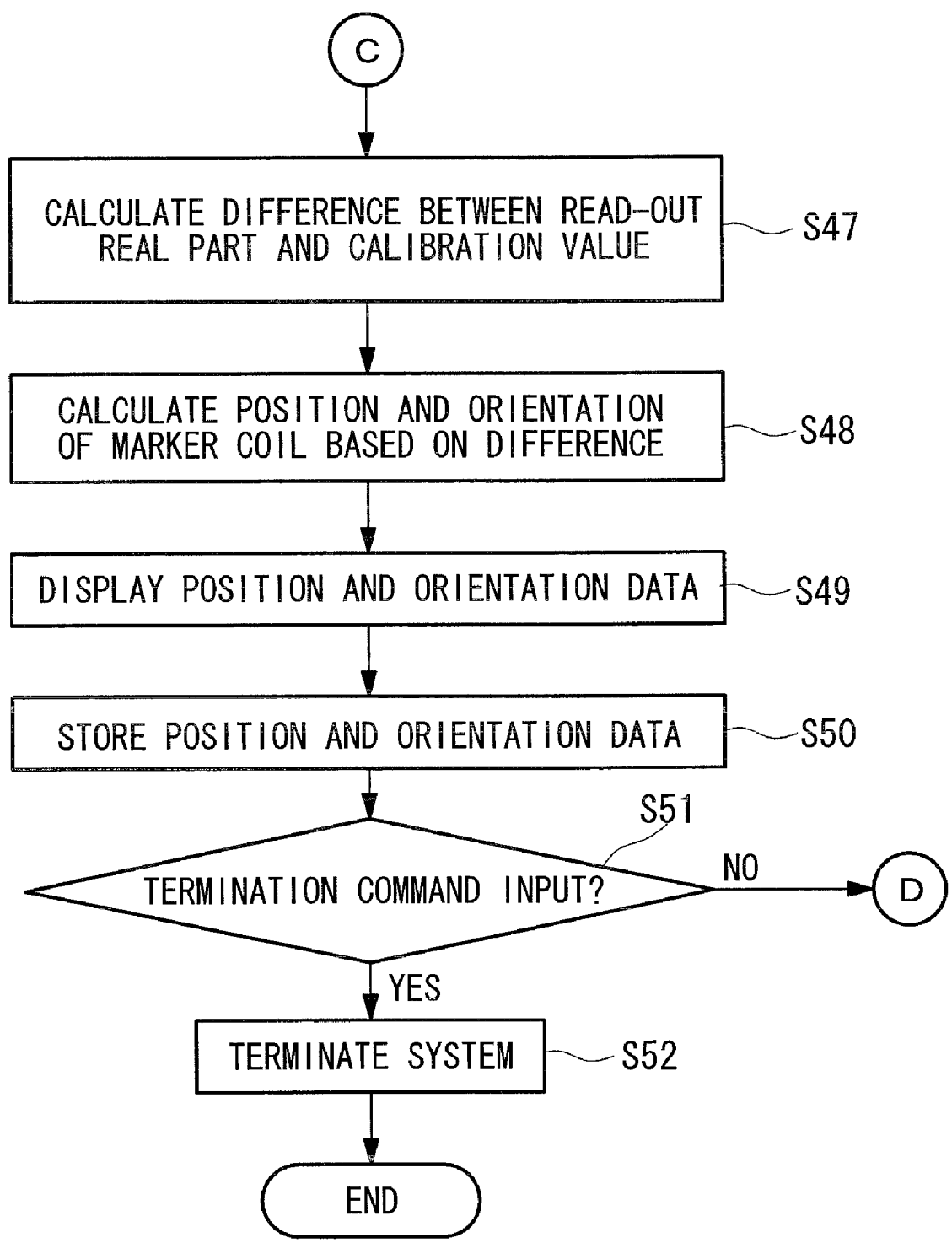
FIG. 8 is a flowchart illustrating actual measurement, continued from FIG. 7.

As shown in FIGS. 6 to 8, actual measurement starts when a command for starting actual measurement is entered on the input device 26 (step S32) with the endoscope apparatus 2 and the capsule medical device 3 being disposed in the body cavity (step S31).

The control circuit 28 instructs the trigger generator 31 to produce a trigger signal for the marker-driving circuit 9 and the read-out-timing generator 30, and the trigger generator 31 produces a trigger signal (step S33).

The marker-driving circuit 9 sequentially generates magnetic-field-generation driving signals in synchronization with the clock signal based on the waveform data stored in the waveform data memory 10 and outputs them to the marker coil 4. The marker coil 4 produces the first alternating magnetic field based on the input magnetic-field-generation driving signals (step S34).

The receiving circuit 13b applies low-pass filtering with a low-pass filter 15, amplification with an amplifier 16, and band-pass filtering with a band-pass filter 17 to a magnetic-field signal associated with the first alternating magnetic field from the marker coil 4 detected by each of the sense coils 13a and then performs A/D conversion in synchronization with the clock signal (step S35).

The magnetic-field signal that has been subjected to A/D conversion is stored in the first memory 19 of the position-calculating section 14 (step S36). Then, it is determined whether or not a number of items of data required to perform frequency analysis processing are accumulated in the first memory 19, and if the required number of items of data are accumulated, frequency analysis processing is performed by the FFT-processing circuit 20 (step S37). Thereafter, it is determined whether or not this frequency analysis processing has been applied to the data from all the sense coils 13a (step S38), and if data from all sense coils 13a have not been processed, steps S32 to S37 are repeated.

When the data from all the sense coils 13a have been subjected to frequency analysis processing, the frequency-selecting section 24 extracts, based on the result of processing, only the magnetic-field information at the frequency of the first alternating magnetic field produced from the marker coil 4 and stores it in the third memory 25, as shown in FIG. 7 (step S39). This processing is applied to the magnetic-field signals from all the sense coils 13a (step S40).

From among the magnetic-field information stored in the third memory 25, the position/orientation analyzing section 22 reads out the imaginary part in the result of frequency analysis processing from the third memory 25 (step S41) and, based on the imaginary part, calculates the position and the orientation of the magnetic induction coil 5 via repeated arithmetic operations (step S42). Because the imaginary part in the result of frequency analysis processing includes only the magnetic-field signal (the second detection-magnetic-field component) of the induced magnetic field produced in the magnetic induction coil 5, i.e., the magnetic-field signal having the first position-calculating frequency $f_0$, which is the same as that of the first alternating magnetic field produced by the marker coil 4, and having a phase shifted by $\pi/2$ relative to the phase of the first alternating magnetic field, the position and the orientation of the magnetic induction coil 5 can be calculated with high accuracy by extracting and using this imaginary part.

The calculated position and orientation of the magnetic induction coil 5 are sent to the control circuit 28, displayed on the display device 8 (step S43), and stored in the second memory 23 (step S44).

Furthermore, the position/orientation analyzing section 22 reads out the real parts in the results of frequency analysis processing of the magnetic-field signals from all the sense coils 13a, as well as the stored calibration values (steps S45 and S46), and calculates the difference values, as shown in FIG. 8 (step S47). Then, based on the calculated difference values, the position and the orientation of the marker coil 4 are calculated via repeated arithmetic operations (step S48).

Because the real part in the result of frequency analysis processing includes only the magnetic-field signal (the first detection-magnetic-field component) having the first position-calculating frequency $f_0$, which is the same as that of the first alternating magnetic field produced by the marker coil 4, and having the same phase as that of the first alternating magnetic field, the position and the orientation of the marker coil 4 can be calculated with high accuracy by extracting and using this real part, without being affected by the capsule medical device 3, even if the capsule medical device 3 is present within a range of detection of the sense coils 13a.

Furthermore, because the position and the orientation of the marker coil 4 are calculated based on the differences obtained by subtracting the calibration values from the real parts in the results of the frequency analysis processing, the influence of magnetic fields originating from other than the capsule medical device 3 can be eliminated, thereby making it possible to calculate the position and the orientation of the marker coil 4 with even higher accuracy.

The calculated position and orientation of the marker coil 4 are sent to the control circuit 28, displayed on the display device 8 (step S49), and stored in the second memory 23 (step S50).

Then, it is checked whether or not a command for terminating position detection has been input on the input device 26 (step S51), and if a command has been input, generation of a trigger signal from the trigger generator 31 is terminated to stop the operation of the position detection system 1 (step S52). On the other hand, if no termination command has been input, the flow returns to step S33 to continue position detection.

In this case, for the initial values for repeated arithmetic operations of the positions and orientations of the magnetic induction coil 5 and the marker coil 4, the calculation results of the positions and the orientations of the magnetic induction coil 5 and the marker coil 4 that have previously been calculated and stored in the second memory 23 are used. By doing so, the convergence time of repeated arithmetic operations can be reduced to calculate the positions and the orientations in a shorter period of time.

In this manner, according to the position detection system 1 of this embodiment and a position detection method using the system 1, the signal from the marker coil 4 and the signal from the magnetic induction coil 5 can be completely separated from each other based on position information of both the signals. Consequently, the positions and orientations of the marker coil 4 and the magnetic induction coil 5, namely, the positions and orientations of the tip of the inserting section 2a of the endoscope apparatus 2 and the capsule medical device 3 disposed in the body cavity, can be obtained accurately.

Second Embodiment

A position detection system 40 according to a second embodiment of the present invention will now be described with reference to FIGS. 9 to 17.

In the description of this embodiment, the same components as those of the position detection system 1 according to the first embodiment are denoted by the same reference numerals, and thus an explanation thereof will be omitted.

Figure 9:
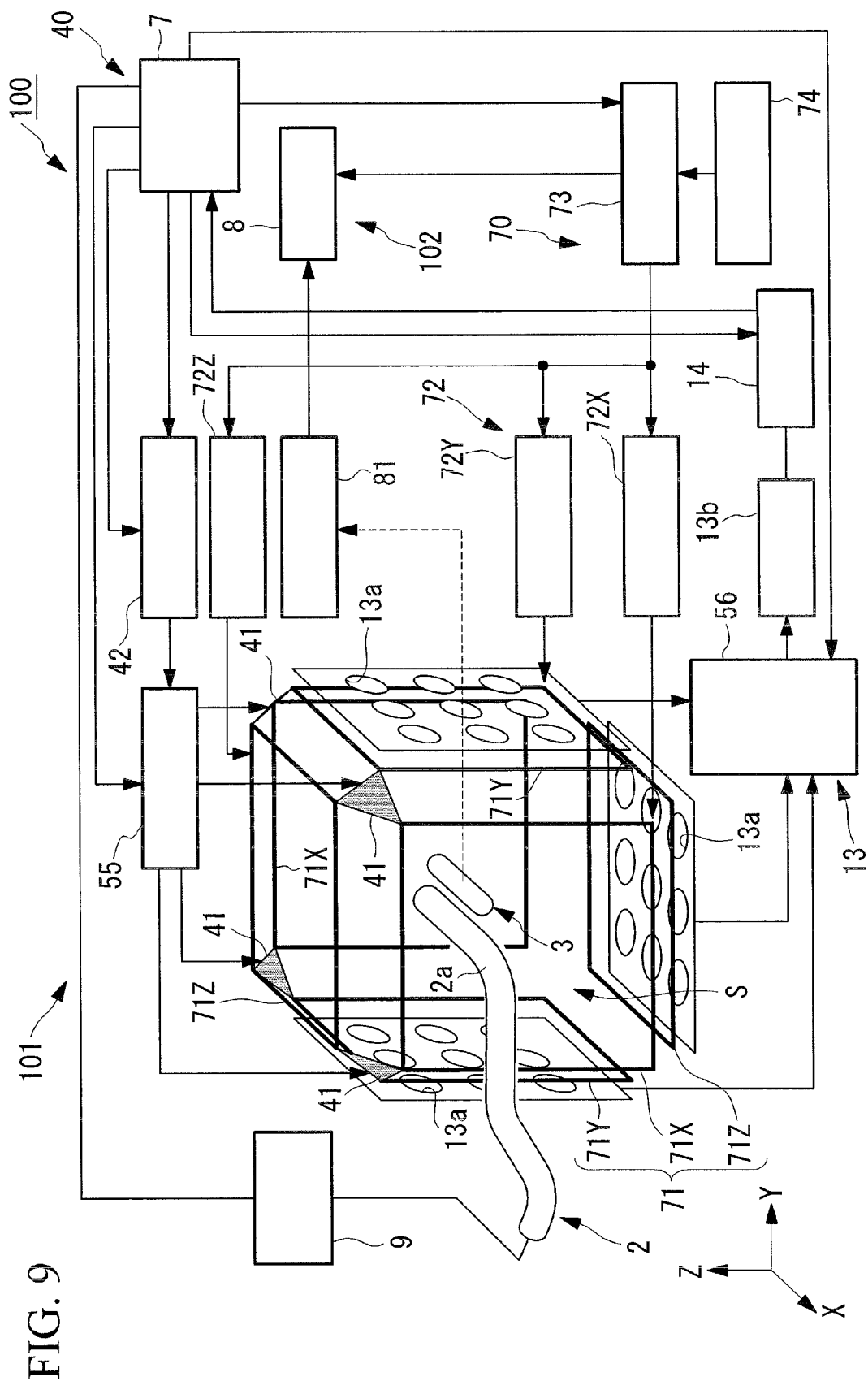
FIG. 9 is a diagram depicting the overall structure of a medical-device guidance system including a position detection system according to a second embodiment of the present invention.

As shown in FIG. 9, the position detection system 40 according to this embodiment is provided in a medical-device guidance system 100. The medical-device guidance system 100 includes the endoscope apparatus 2 and the capsule medical device 3 that are introduced, per oral or per anus, into the body cavity of a subject; the position detection system 40; a magnetic induction apparatus 101 that guides the capsule medical device 3 based on the detected position and the orientation and an operator instruction; and an image display device 102 that displays an image signal transmitted from the capsule medical device 3.

As shown in FIG. 9, the magnetic induction apparatus 101 includes a three-axis Helmholtz coil unit (propulsion-magnetic-field generating unit) 71 that produces parallel external magnetic fields (rotating magnetic fields) for driving the capsule medical device 3; a Helmholtz-coil driver 72 that amplifies and controls an electrical current to be supplied to the three-axis Helmholtz coil unit 71; a magnetic field control circuit (propulsion-magnetic-field control section) 73 that controls the directions of the external magnetic fields for driving the capsule medical device 3; and an input device 74 that outputs to the magnetic field control circuit 73 the direction of movement of the capsule medical device 3 input by the operator.

Although the term "three-axis Helmholtz coil unit 71" is used in this embodiment, it is not necessary that Helmholtz-coil conditions be strictly satisfied. For example, the coils need not be circular but may be substantially rectangular, as shown in FIG. 9. Furthermore, the gaps between opposing coils do not need to satisfy Helmholtz-coil conditions, as long as the function of this embodiment is achieved.

As shown in FIG. 9, the three-axis Helmholtz coil unit 71 is formed in a substantially rectangular shape. In addition, the three-axis Helmholtz coil unit 71 includes three-pairs of mutually opposing Helmholtz coils (electromagnets) 71X, 71Y, and 71Z, and each pair of Helmholtz coils 71X, 71Y, and 71Z is disposed so as to be substantially orthogonal to the X, Y, and Z axes in FIG. 9. The Helmholtz coils disposed substantially orthogonally with respect to the X, Y, and Z axes are denoted as the Helmholtz coils 71X, 71Y, and 71Z, respectively.

Furthermore, the Helmholtz coils 71X, 71Y, and 71Z are disposed so as to form a substantially rectangular space S in the interior thereof. As shown in FIG. 9, the space S serves as a working space (also referred to as the working space S) of the capsule medical device 3 and is the space in which the subject is placed.

The Helmholtz-coil driver 72 includes Helmholtz-coil drivers 72X, 72Y, and 72Z for controlling the Helmholtz coils 71X, 71Y, and 71Z, respectively.

The magnetic field control circuit 73 receives from the position detection system 40 (described later) data representing the current orientation of the capsule medical device 3 (the direction along the longitudinal axis R of the capsule medical device 3), as well as a direction-of-movement command for the capsule medical device 3 input by the operator on the input device 74. Then, signals for controlling the Helmholtz-coil drivers 72X, 72Y, and 72Z are output from the magnetic field control circuit 73, rotational phase data of the capsule medical device 3 is output to an image display device 102, and electrical current data to be supplied to each of the Helmholtz-coil drivers 72X, 72Y, and 72Z is output.

Furthermore, for example, a joystick (not shown in the figure) is provided as the input device 74, so that the movement direction of the capsule medical device 3 can be specified by operating the joystick.

As mentioned above, for the input device 74, a joystick-type device may be used, or another type of input device may be used, such as an input device that specifies the direction of movement by pushing direction-of-movement buttons.

Figure 10:
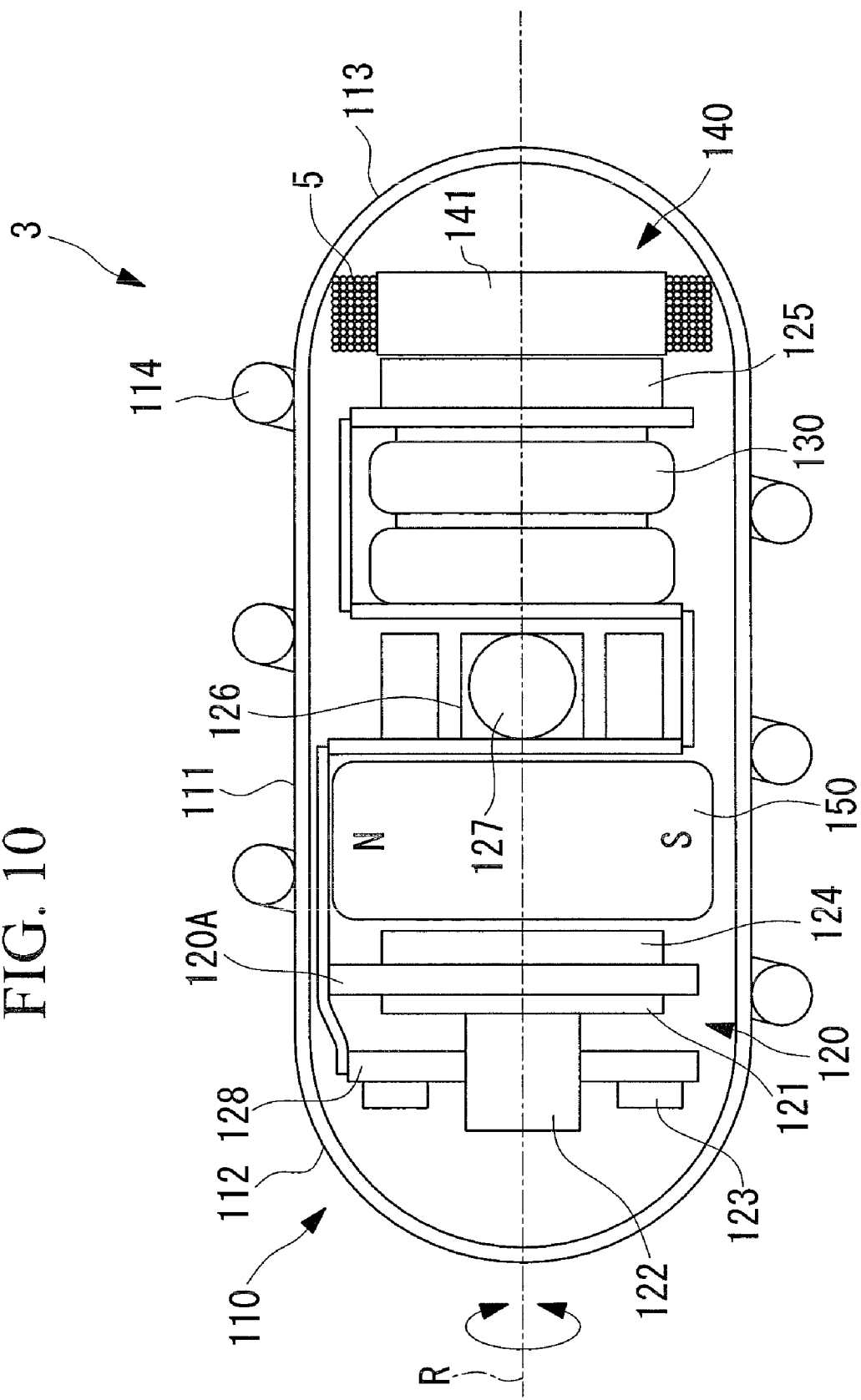
FIG. 10 is a longitudinal sectional view of one example of a capsule medical device used in the medical-device guidance system shown in FIG. 9.

As shown in FIG. 10, the capsule medical device 3 includes an outer casing 110 accommodating various types of devices therein; an imaging section 120 that acquires an image of the internal surface of a passage in the body cavity of a subject I; a battery 130 that powers the imaging section 120; an induced-magnetic-field generating unit 140 that produces an alternating magnetic field with a magnetic-field generating device 41 (described later); and a permanent magnet (magnetic-field acting section) 150 that drives the capsule medical device 3 in response to the external magnetic field produced by a magnetic induction apparatus 70.

The outer casing 110 includes an infrared-transmitting cylindrical capsule main body (hereinafter, referred to simply as the "main body") 111 whose central axis is defined by the longitudinal axis R of the capsule medical device 3; a transparent, hemispherical front end portion 112 covering the front end of the main body 111; and a hemispherical rear end portion 113 covering the rear end of the main body, to form a sealed capsule container with a watertight construction.

A helical part 114 made of a wire having a circular cross-section is helically wound about the longitudinal axis R over the outer circumferential surface of the main body 111 of the outer casing 110.

When the permanent magnet 150 is rotated in response to the rotating external magnetic field produced by the magnetic induction apparatus 70, the helical part 114 is rotated about the longitudinal axis R along with the main body 111. As a result, the rotational motion about the longitudinal axis R of the main body 111 is transformed into a linear motion in the direction along the longitudinal axis R by means of the helical part 114, thereby making it possible to guide the capsule medical device 3 in the direction along the longitudinal axis R in the body passage.

The imaging section 120 includes a board 120A disposed substantially orthogonal to the longitudinal axis R; an image sensor 121 disposed on the surface of the board 120A adjacent to the front end portion 112; a lens group 122 that focuses an image of an internal surface of a passage in the body cavity of the subject at the image sensor 121; an LED (light emitting diode) 123 that emits light onto the internal surface of the passage in the body cavity; a signal processing unit 124 disposed on the surface of the board 120A adjacent to the rear end portion 113; and a radio device 125 that transmits an image signal to the image display device 102.

The signal processing unit 124 is electrically connected to the battery 130, the image sensor 121, and the LED 123. Also, the signal processing unit 124 compresses the image signal acquired by the image sensor 121, temporarily stores it (memory), and transmits the compressed image signal to the exterior from the radio device 125, and in addition, it controls the on/off state of the image sensor 121 and the LED 123 based on signals from a switch unit 126 to be described later.

The image sensor 121 converts the image formed via the front end portion 112 and the lens group 122 into an electrical signal (image signal) and outputs it to the signal processing unit 124. A CMOS (Complementary Metal Oxide Semiconductor) device or a CCD, for example, can be used as this image sensor 121.

Moreover, a plurality of the LEDs 123 is disposed on a support member 128 positioned towards the front end portion 112 from the board 120A such that gaps are provided therebetween in the circumferential direction around the longitudinal axis R.

The image display device 102 includes an image receiving circuit 81 that receives image data sent from the capsule medical device 3 and the display device 8 that displays the received image data.

The permanent magnet 150 is disposed towards the rear end portion 113 from the signal processing unit 124. The permanent magnet 150 is disposed or polarized so as to have a magnetization direction (magnetic pole) in a direction orthogonal to the longitudinal axis R.

The switch unit 126 is disposed at the side, adjacent to the rear end portion 113, of the permanent magnet 150. The switch unit 126 includes an infrared sensor 127 and is electrically connected to the signal processing unit 124 and the battery 130.

Also, a plurality of the switch units 126 are disposed in the circumferential direction about the longitudinal axis R at regular intervals, and the infrared sensor 127 is disposed so as to face the outside in the diameter direction. In this embodiment, an example has been described in which four switch units 126 are disposed, but the number of switch units 126 is not limited to four; any number may be provided.

The induced-magnetic-field generating unit 140, which is disposed at the side adjacent to the rear end portion 113 of the radio device 125, is composed of a core member (magnetic core) 141 made of ferrite formed in the shape of a cylinder whose central axis is substantially aligned with the longitudinal axis R, the magnetic induction coil 5 disposed at the outer circumferential part of the core member 141, and a capacitor (not shown in the figure) that is electrically connected to the magnetic induction coil 5 and that constitutes the resonance circuit.

In addition to ferrite, magnetic materials are suitable for the core member 141; iron, nickel, permalloy, cobalt or the like may be used for the core member.

Figure 11:
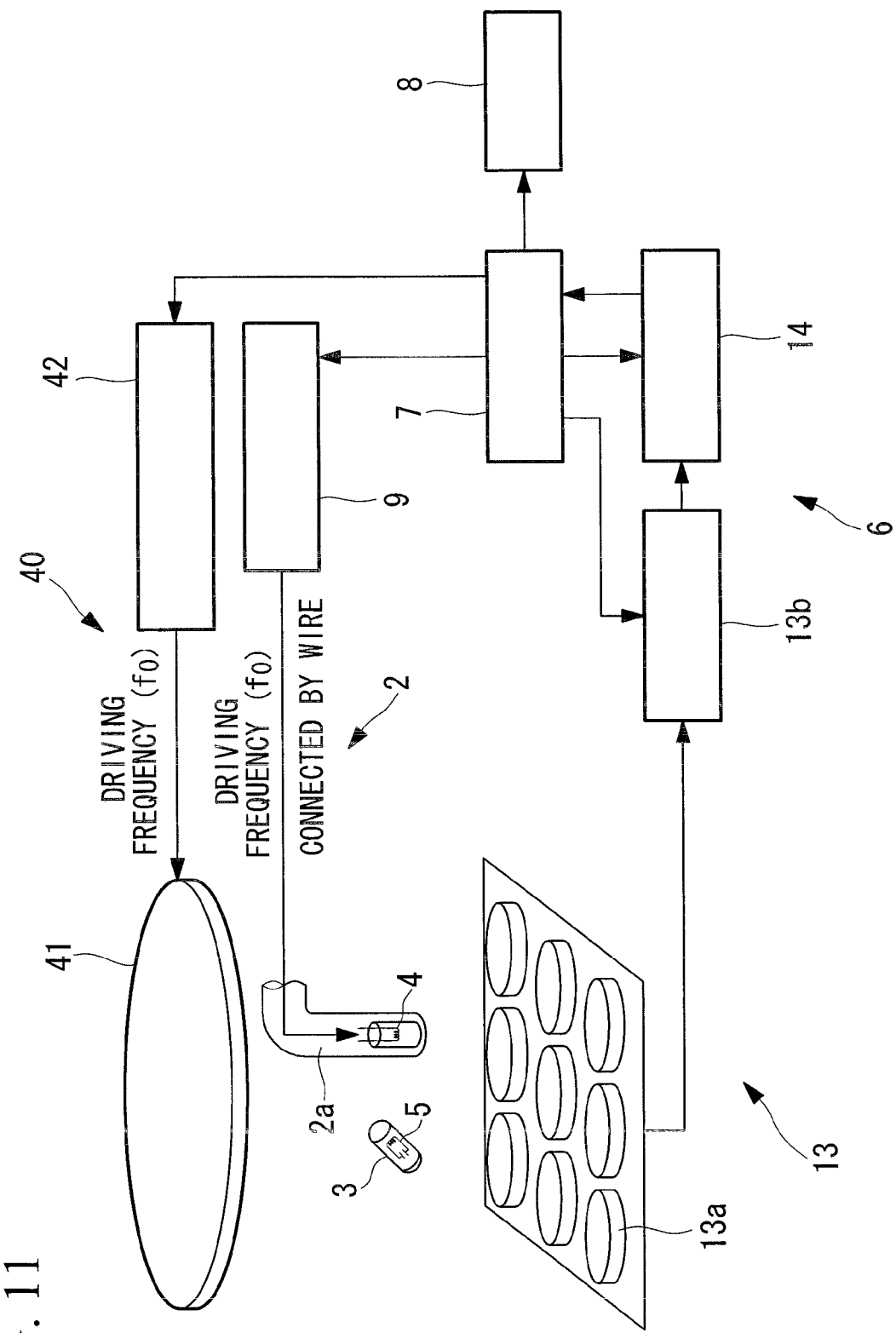
FIG. 11 is a block diagram depicting the overall structure of the position detection system according to this embodiment, provided in the medical-device guidance system shown in FIG. 9.
Figure 12:
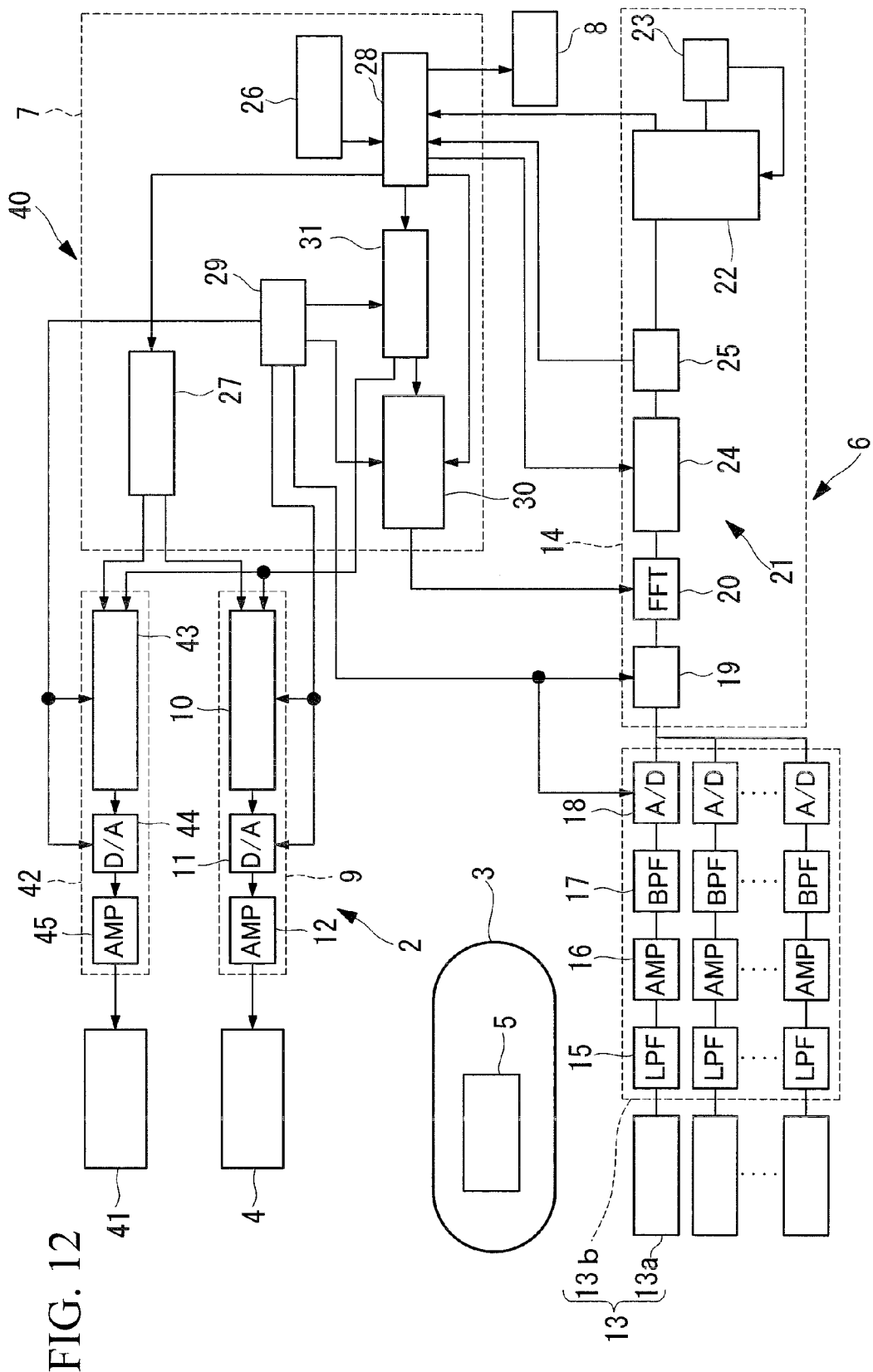
FIG. 12 is a block diagram depicting the detailed structure of the position detection system shown in FIG. 11.

As shown in FIGS. 9 to 12, the position detection system 40 according to this embodiment differs from the position detection system 1 according to the above-described first embodiment in that the position detection system 40 includes the magnetic-field generating device 41 that is disposed outside a working region of the magnetic induction coil 5 and that produces a second alternating magnetic field having the above-described first position-calculating frequency $f_0$ and having the same phase as that of the above-described first alternating magnetic field, as well as a magnetic-field-generating-device driving circuit 42. The system 40 also differs from the system 1 in arithmetic operations in the position/orientation analyzing section 22. In FIG. 12, reference numeral 43 denotes a waveform data memory, reference numeral 44 denotes a D/A converter, reference numeral 45 denotes an amplifier, reference numeral 55 denotes a selector that selects the magnetic-field generating device 41, and reference numeral 56 denotes a sense-coil selector that selects the sense coils 13a.

FIGS. 11 and 12 depict a simplified structure of the position detection system 40 according to this embodiment.

In order to detect the positions and the orientations of the marker coil 4 at the tip of the endoscope apparatus 2 and the magnetic induction coil 5 in the capsule medical device 3 by using the position detection system 40 according to this embodiment, waveform data of the produced first and second alternating magnetic fields is generated in the same manner as in the first embodiment and is stored in the waveform data memories 10 and 43, and then calibration is carried out with the capsule medical device 3 being disposed outside the working region.

Because not only is the first alternating magnetic field produced from the marker coil 4 but also the second alternating magnetic field is produced from the magnetic-field generating device 41, the generated items of magnetic field waveform data are transferred to the waveform data memories 10 and 43 of the marker-driving circuit 9 and the magnetic-field-generating-device driving circuit 42, respectively. The first and second alternating magnetic fields produced from the marker coil 4 and the magnetic-field generating device 41 correspond in terms of the first position-calculating frequency $f_0$, which is the resonance frequency of the magnetic induction coil 5, and have the same phase.

Figure 13:
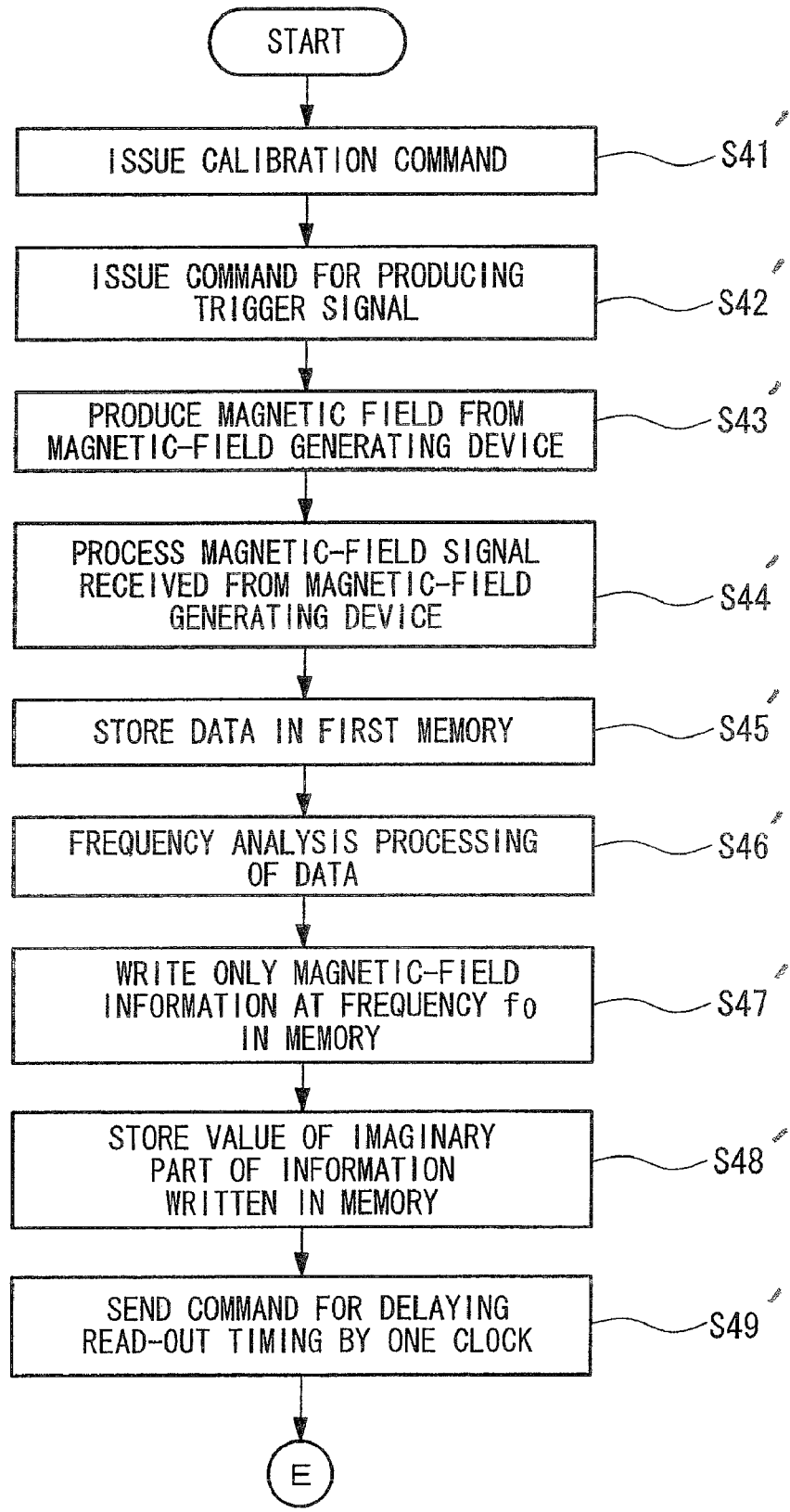
FIG. 13 is a flowchart illustrating the first-half stage of calibration by a position detection method using the position detection system shown in FIG. 11.
Figure 14:
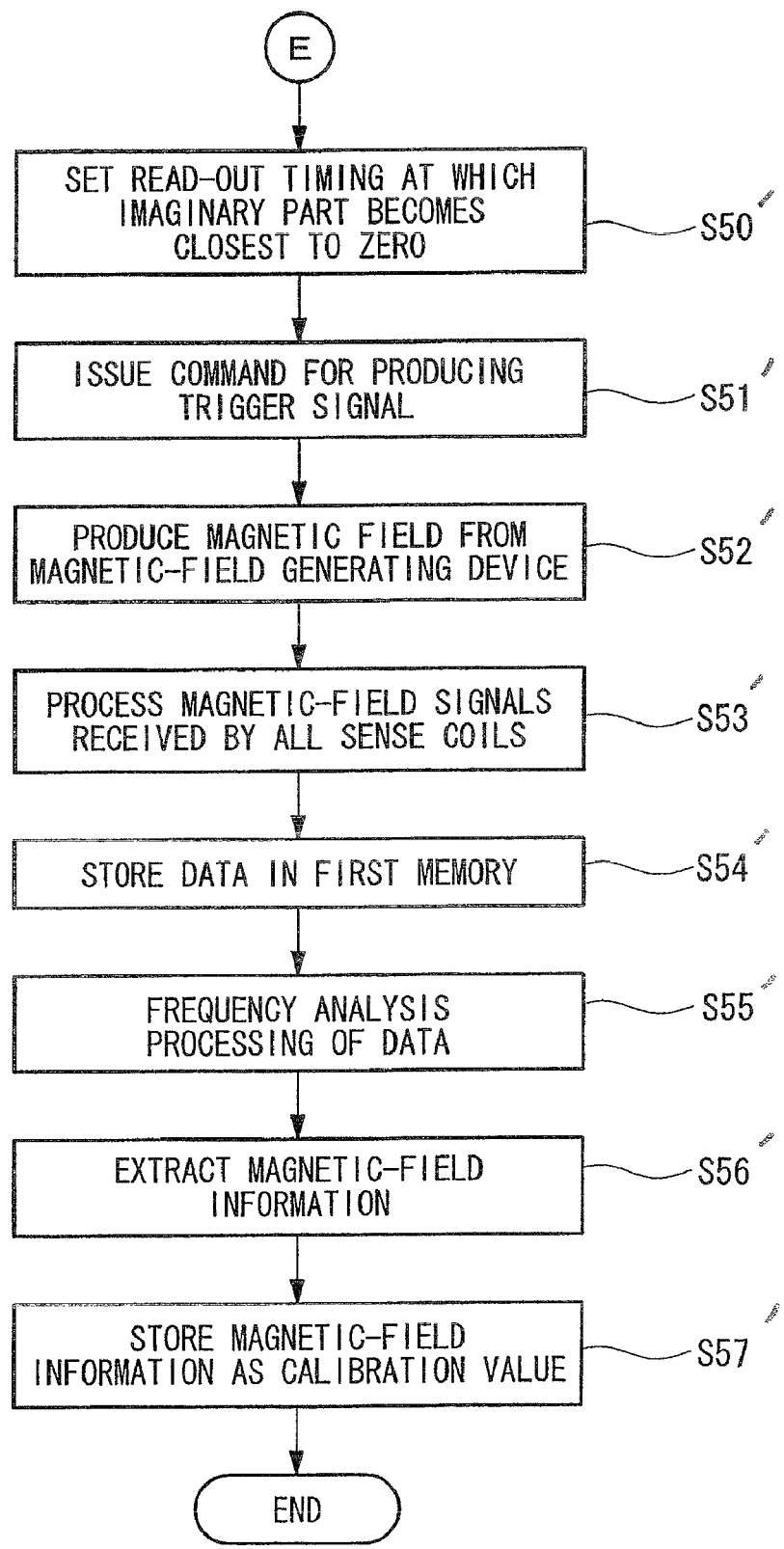
FIG. 14 is a flowchart illustrating the second-half stage of calibration, continued from FIG. 13.
Figure 15:
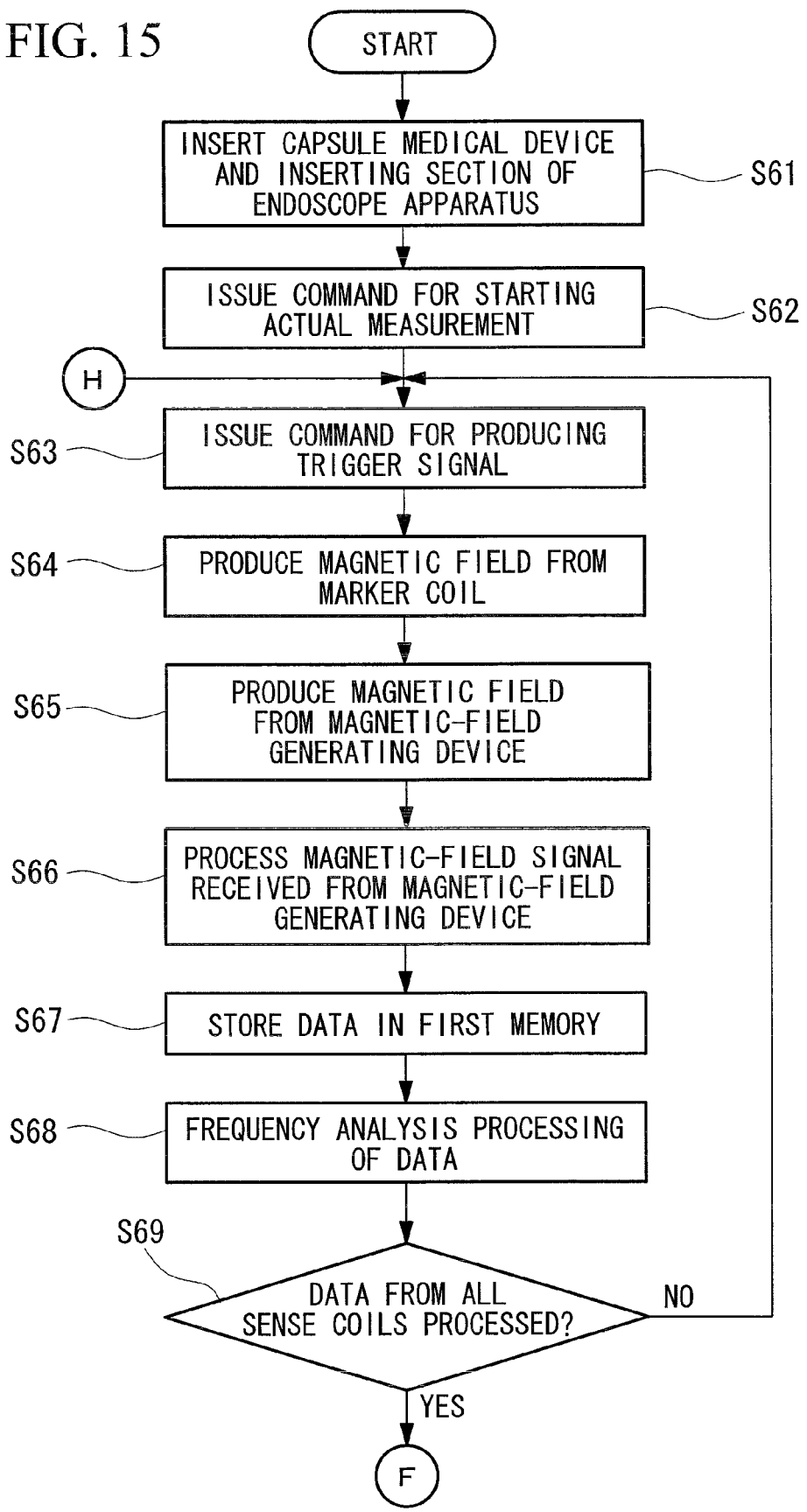
FIG. 15 is a flowchart illustrating the first-half stage of actual measurement by the position detection system of FIG. 11.

As shown in FIGS. 13 and 14, calibration starts when a calibration command is input from the input device 26 while the tip of the inserting section 2a of the endoscope apparatus 2 is disposed in the body cavity and the capsule medical device 3 is not disposed in the body cavity (step S41'). The control circuit 28 instructs the trigger-signal generator 31 to produce a trigger signal for the magnetic-field-generating-device driving circuit 42 and the read-out-timing generator 30. By doing so, a trigger signal is issued from the trigger-signal generator 31 (step S42').

Based on the waveform data stored in the waveform data memory 43, the magnetic-field-generating-device driving circuit 42 that has received the trigger signal sequentially generates magnetic-field-generation driving signals in synchronization with the clock signal from the clock 29 and outputs them to the magnetic-field generating device 41. The magnetic-field generating device 41 produces the second alternating magnetic field based on the input magnetic-field-generation driving signals (step S43').

The receiving circuit 13b receives a magnetic-field signal associated with the second alternating magnetic field from the magnetic-field generating device 41 detected by each of the sense coils 13a; performs low-pass filtering, amplification, and band-pass filtering; and then performs A/D conversion in synchronization with the clock signal (step S44').

The magnetic-field signal that has been subjected to A/D conversion is stored in the first memory 19 of the position-calculating section 14 (step S45'). Thereafter, it is determined whether or not a number of items of data required to perform frequency analysis processing are accumulated in the first memory 19, and if the required number of items of data are accumulated, frequency analysis processing is performed by the FFT-processing circuit 20 (step S46').

Based on the result of frequency analysis processing, the frequency-selecting section 24 extracts only the magnetic-field information at the first position-calculating frequency $f_0$, which is the frequency of the second alternating magnetic field produced from the magnetic-field generating device 41, and stores it in the third memory 25 (step S47').

The control circuit 28 reads out the magnetic-field information stored in the third memory 25 and stores the value of the imaginary part (step S48').

Then, the control circuit 28 sends to the read-out-timing generator 30 a command for delaying by one clock the read-out timing to be generated in the read-out-timing generator 30 (step S49').

Thereafter, steps S42' to S49' are repeated, and the read-out timing that causes the value of the imaginary part in the result of frequency analysis processing stored at step S48' to become closest to zero is set in the read-out-timing generator 30 as read-out timing used for actual measurement (step S50').

Measurement of a calibration value is carried out while the read-out timing that causes the value of the imaginary part in the result of frequency analysis processing to become closest to zero is set in the read-out-timing generator 30 as described above.

More specifically, the control circuit 28 instructs the trigger generator 31 to produce a trigger signal for the magnetic-field-generating-device driving circuit 42 and the read-out-timing generator 30 (step S51'), and based on the waveform data stored in the waveform data memory 43, the magnetic-field-generating-device driving circuit 42 sequentially produces magnetic-field-generation driving signals in synchronization with the clock signal and outputs them to the magnetic-field generating device 41. The magnetic-field generating device 41 produces the second alternating magnetic field based on the input magnetic-field-generation driving signals (step S52').

Next, the receiving circuit 13b applies low-pass filtering, amplification, and band-pass filtering to the magnetic-field signals from the magnetic-field generating device 41 received by all the sense coils 13a and performs A/D conversion in synchronization with the clock signal (step S53'). The magnetic-field signals that have been subjected to A/D conversion are accumulated in the first memory 19 of the position-calculating section 14 (step S54').

Then, the magnetic-field signals detected by all the sense coils 13a are read out from the first memory 19 with the above-described read-out timing and are subjected to frequency analysis processing (step S55'). The real part value, the imaginary part value, and the absolute value of the magnetic-field intensity at the first position-calculating frequency $f_0$ are extracted from the magnetic-field information obtained as a result of frequency analysis processing (step S56'), and the extracted values are stored as calibration values corresponding to the respective sense coils 13a (step S57'). This completes calibration processing, followed by actual measurement.

Next, actual measurement starts when a command for starting actual measurement is entered on the input device 26 (step S62) with the endoscope apparatus 2 and the capsule medical device 3 being disposed in the body cavity (step S61).

The control circuit 28 instructs the trigger generator 31 to produce a trigger signal for the marker-driving circuit 9, the magnetic-field-generating-device driving circuit 42, and the read-out-timing generator 30, and the trigger generator 31 produces a trigger signal (step S63).

The marker-driving circuit 9 sequentially generates magnetic-field-generation driving signals in synchronization with the clock signal based on the waveform data stored in the waveform data memory 10 and outputs them to the marker coil 4. The marker coil 4 produces the first alternating magnetic field based on the input magnetic-field-generation driving signals (step S64).

Furthermore, based on the waveform data stored in the waveform data memory 43, the magnetic-field-generating-device driving circuit 42 sequentially generates magnetic-field-generation driving signals in synchronization with the clock signal and outputs them to the magnetic-field generating device 41. The magnetic-field generating device 41 produces the second alternating magnetic field based on the input magnetic-field-generation driving signals (step S65).

The receiving circuit 13*b* applies low-pass filtering, amplification, and band-pass filtering to a magnetic-field signal associated with the first alternating magnetic field from the marker coil 4 and to a magnetic-field signal associated with the second alternating magnetic field from the magnetic-field generating device 41, i.e., the magnetic-field signals detected by each of the sense coils 13*a*, and then performs A/D conversion in synchronization with the clock signal (step S66).

The magnetic-field signals that have been subjected to A/D conversion are stored in the first memory 19 of the position-calculating section 14 (step S67). Then, it is determined whether or not a number of items of data required to perform frequency analysis processing are accumulated in the first memory 19, and if the required number of items of data are accumulated, frequency analysis processing is performed by the FFT-processing circuit 20 (step S68). Thereafter, it is determined whether or not the data from all the sense coils 13*a* have been subjected to this frequency analysis processing (step S69). If data from all sense coils 13*a* have not been processed, steps S63 to S68 are repeated.

Figure 16:
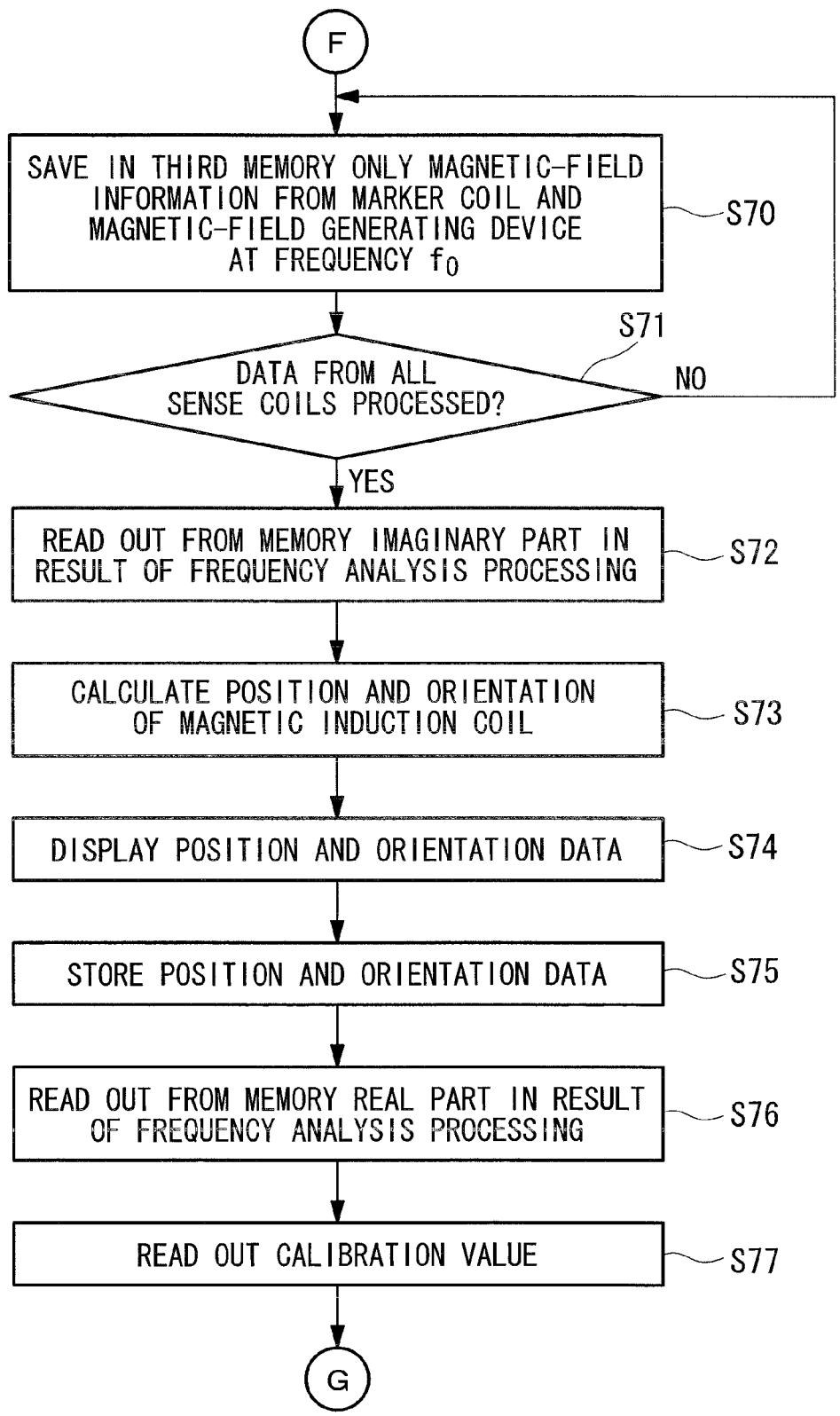
FIG. 16 is a flowchart illustrating actual measurement, continued from FIG. 15.
Figure 17:
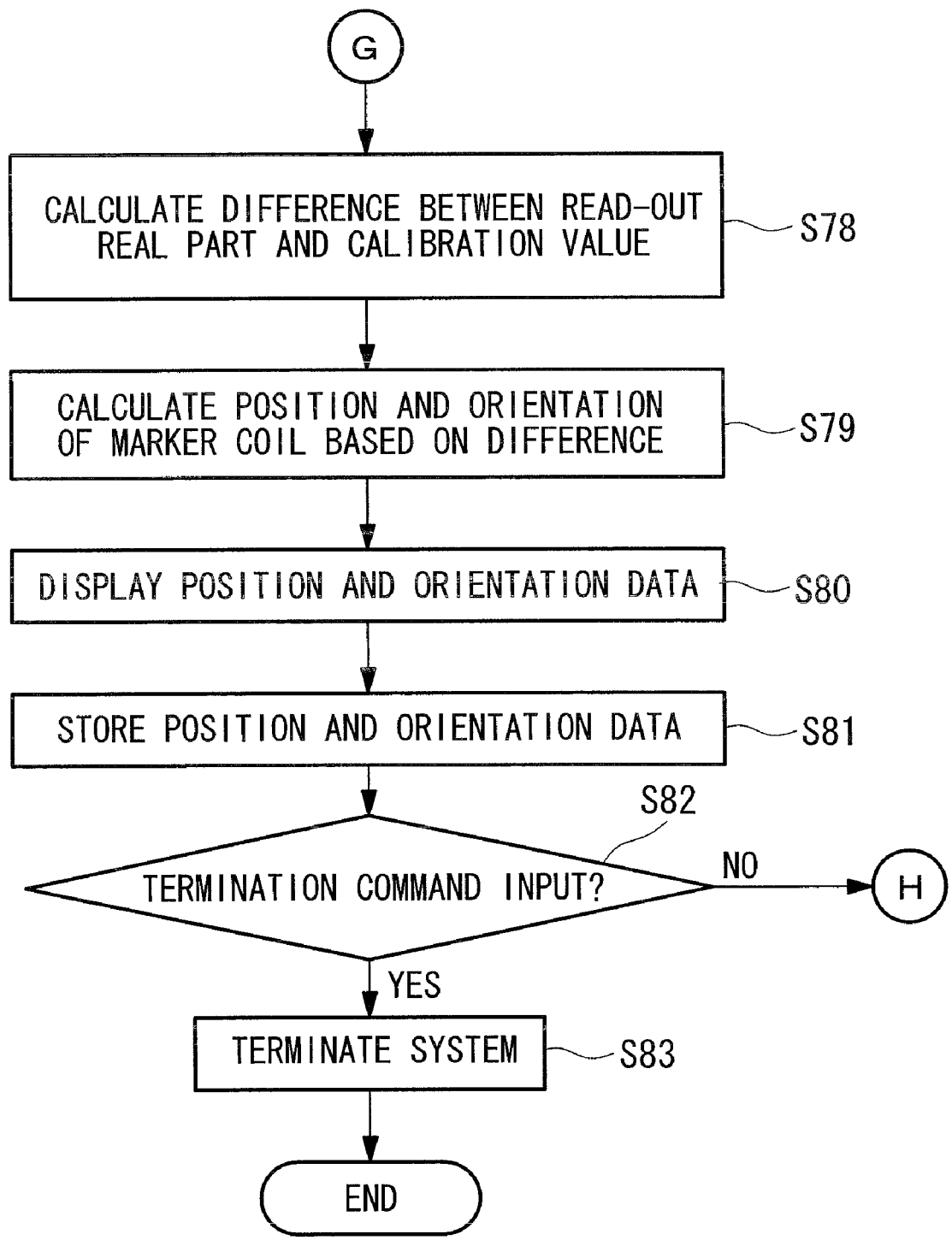
FIG. 17 is a flowchart illustrating actual measurement, continued from FIG. 16.

When the data from all the sense coils 13*a* have been subjected to frequency analysis processing, the frequency-selecting section 24 extracts, based on the result of processing, only the magnetic-field information at the frequency of the first alternating magnetic field produced from the marker coil 4 and the magnetic-field information at the frequency of the second alternating magnetic field produced from the magnetic-field generating device 41, as shown in FIG. 16, and stores it in the third memory 25 (step S70). This processing is applied to the magnetic-field signals from all the sense coils 13*a* (step S71).

From among the magnetic-field information stored in the third memory 25, the position/orientation analyzing section 22 first reads out the imaginary part in the result of frequency analysis processing from the third memory 25 (step S72) and, based on the imaginary part, calculates the position and the orientation of the magnetic induction coil 5 via repeated arithmetic operations (step S73). Because the imaginary part in the result of frequency analysis processing includes only the magnetic-field signal (the second detection-magnetic-field component) of the induced magnetic field produced in the magnetic induction coil 5, i.e., the magnetic-field signal having the first position-calculating frequency $f_0$, which is the same as that of the first and second alternating magnetic fields produced by the marker coil 4, and having a phase shifted by $\pi/2$ relative to the phase of the first and second alternating magnetic fields, the position and the orientation of the magnetic induction coil 5 can be calculated with high accuracy by extracting and using this imaginary part.

The calculated position and orientation of the magnetic induction coil 5 are sent to the control circuit 28, displayed on the display device 8 (step S74), and stored in the second memory 23 (step S75).

Furthermore, the position/orientation analyzing section 22 reads out the real parts in the results of frequency analysis processing of the magnetic-field signals from all the sense coils 13*a*, as well as the real part (stored as a calibration value) in the result of frequency analysis processing of the magnetic-field signal from each of the sense coils 13*a* while only the second alternating magnetic field from the magnetic-field generating device 41 is present (steps S76 and S77), to calculate the difference value (step S78). Then, based on the calculated difference values, the position and the orientation of the marker coil 4 are calculated via repeated arithmetic operations (step S79).

Because the real part in the result of frequency analysis processing includes only the magnetic-field signal (the first detection-magnetic-field component) having the first position-calculating frequency $f_0$, which is the same as that of the first and second alternating magnetic fields, and having the same phase as that of the first alternating magnetic field, the position and the orientation of the marker coil 4 can be calculated with high accuracy by extracting and using this real part, without being affected by the magnetic induction coil 5 of the capsule medical device 3, even if the capsule medical device 3 is present within the range of detection of the sense coils 13*a*.

In addition, because the position and the orientation of the marker coil 4 are calculated based on the difference obtained by subtracting the real part, as a calibration value, in the result of frequency analysis processing of the magnetic-field signal from each of the sense coils 13*a* while only the second alternating magnetic field is acting, the position and the orientation of the marker coil 4 can be calculated with even higher accuracy by disabling the magnetic field from the magnetic-field generating device 41.

The calculated position and orientation of the marker coil 4 are sent to the control circuit 28, displayed on the display device 8 (step S80), and stored in the second memory 23 (step S81).

Then, it is checked whether or not a command for terminating position detection has been input on the input device 26 (step S82), and if a command has been input, generation of a trigger signal from the trigger generator 31 is terminated to stop the operation of the position detection system 1 (step S83). On the other hand, if no termination command has been input, the flow returns to step S63 to continue position detection.

In this case, for the initial values for repeated arithmetic operations of the positions and orientations of the marker coil 4 and the magnetic induction coil 5, the calculation results of the positions and the orientations of the marker coil 4 and the magnetic induction coil 5 that have previously been calculated and stored in the second memory 23 are used. By doing so, the convergence time of repeated arithmetic operations can be reduced to calculate the positions and the orientations in a shorter period of time.

As described above, according to the position detection system 40 of this embodiment and the position detection method using the system 40, the positions and/or the orientations of the endoscope apparatus 2 and the capsule medical device 3 can be calculated simultaneously with high accuracy, even when the endoscope apparatus 2 having the marker coil 4 that produces a magnetic field by means of external power supply and the capsule medical device 3 having the magnetic induction coil 5 coexist. In addition to the first alternating magnetic field, the second alternating magnetic field also produces an induced magnetic field from the second marker, and therefore the intensity of the induced magnetic field can be increased.

Third Embodiment

A position detection system 50 according to a third embodiment of the present invention will now be described with reference to FIGS. 18 to 24.

In the description of this embodiment, the same components as those of the position detection system 40 according to the second embodiment are denoted by the same reference numerals, and thus an explanation thereof will be omitted.

Figure 18:
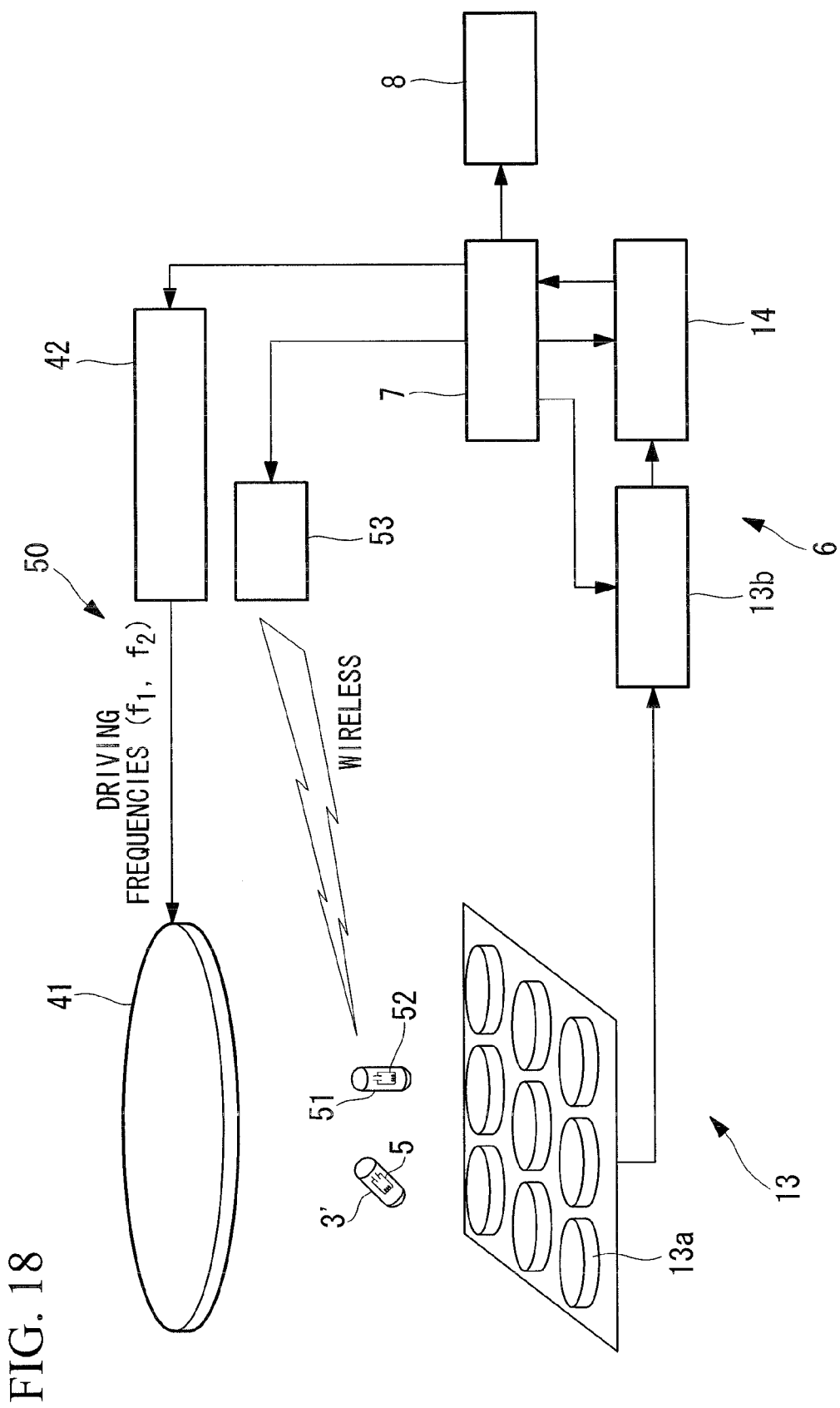
FIG. 18 is a block diagram depicting the overall structure of a position detection system according to a third embodiment of the present invention.

As shown in FIG. 18, the position detection system 50 according to this embodiment differs from the position detection system 40 according to the above-described second embodiment in the following points: a marker coil 52 is disposed in a first capsule medical device 51 in place of the marker coil 4 provided at the tip of the endoscope apparatus 2; a transmission section 53 that sends a signal to the relevant first capsule medical device 51 is provided; the magnetic induction coil 5 is disposed in a second capsule medical device 3'; the second alternating magnetic field produced by the magnetic-field generating device 41 has a different frequency; and arithmetic operations in the position-calculating section 14.

Figure 19:
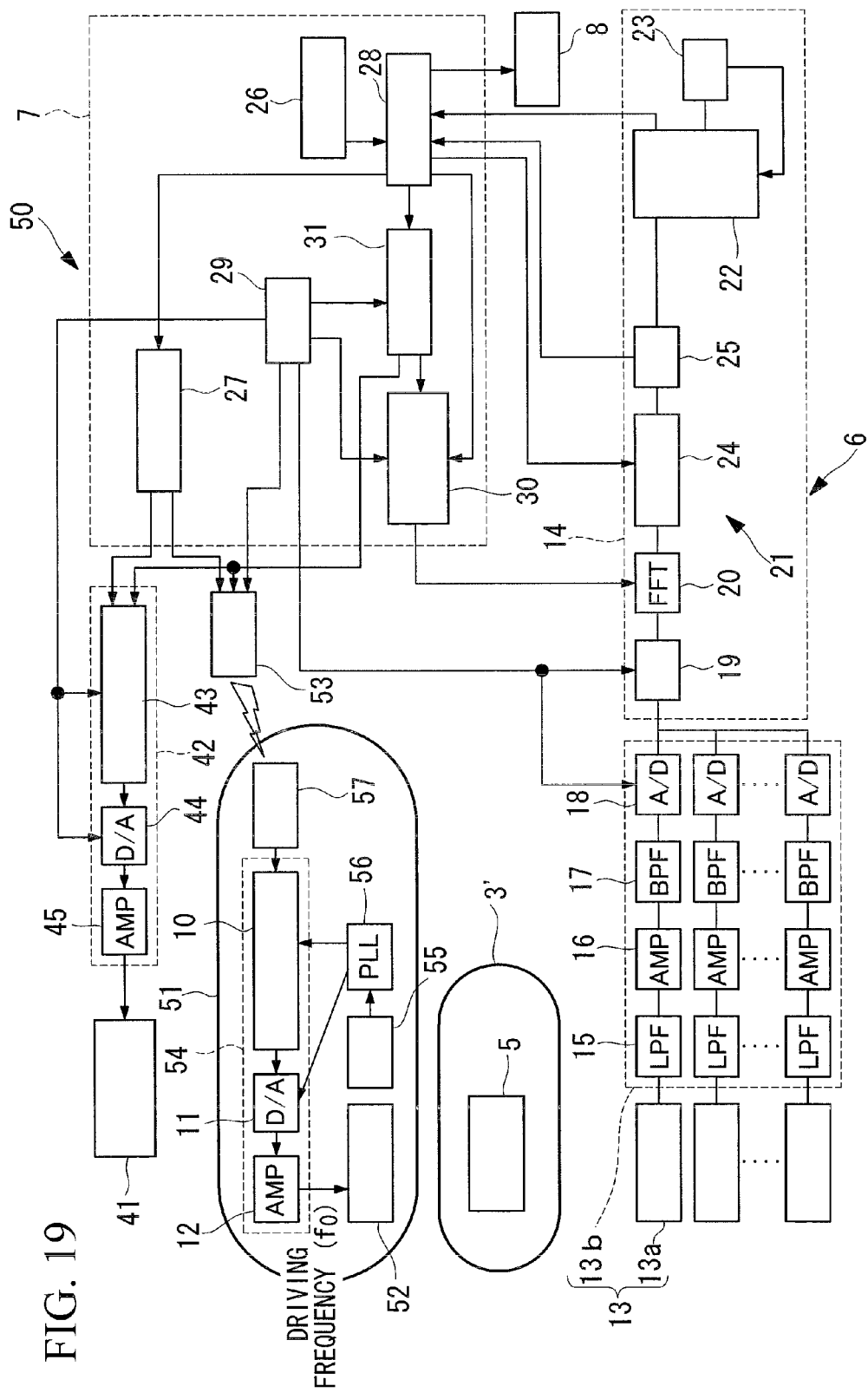
FIG. 19 is a block diagram depicting the detailed structure of the position detection system shown in FIG. 18.
Figure 20:
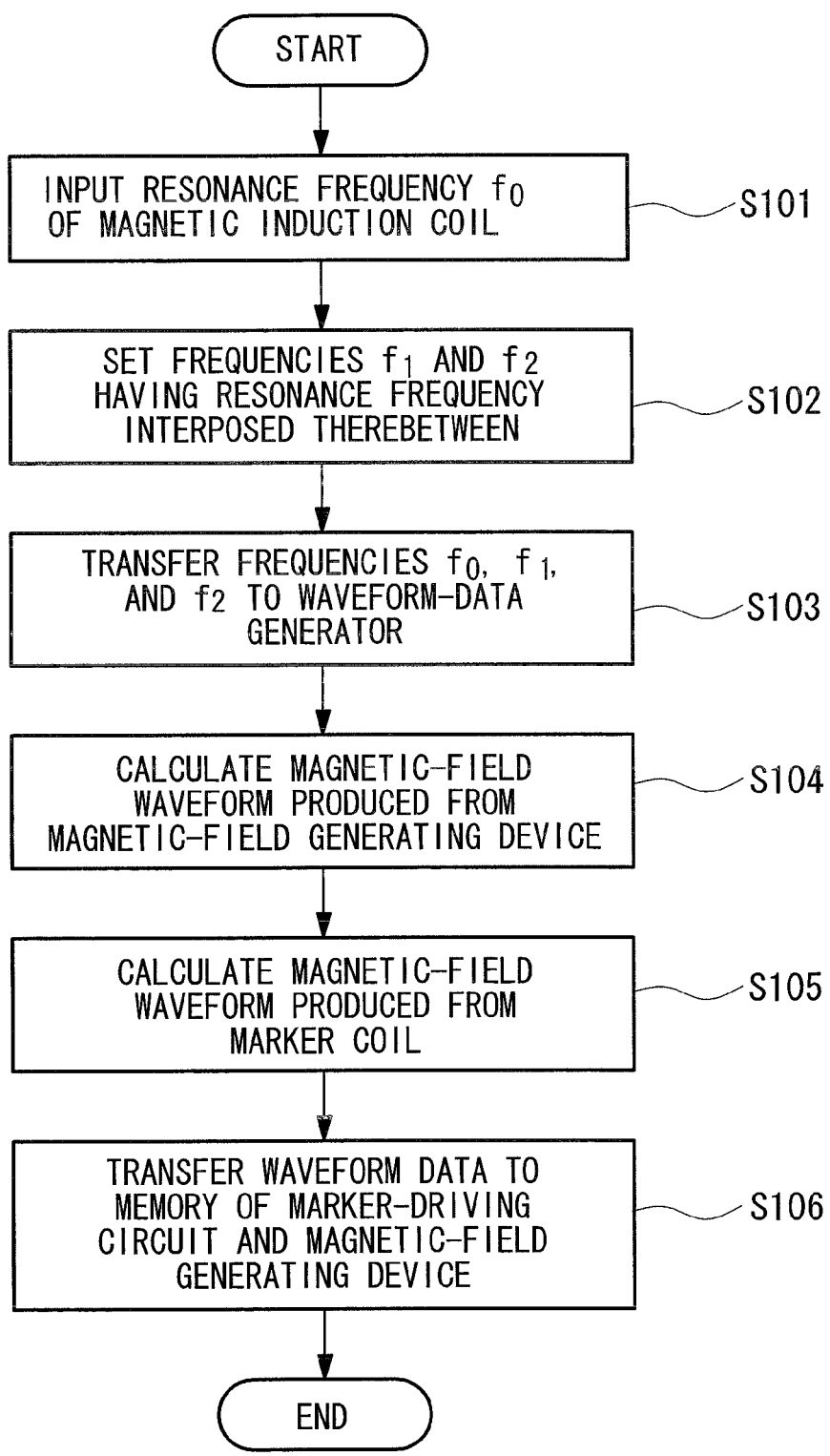
FIG. 20 is a flowchart illustrating waveform generation by a position detection method using the position detection system shown in FIG. 18.
Figure 21:
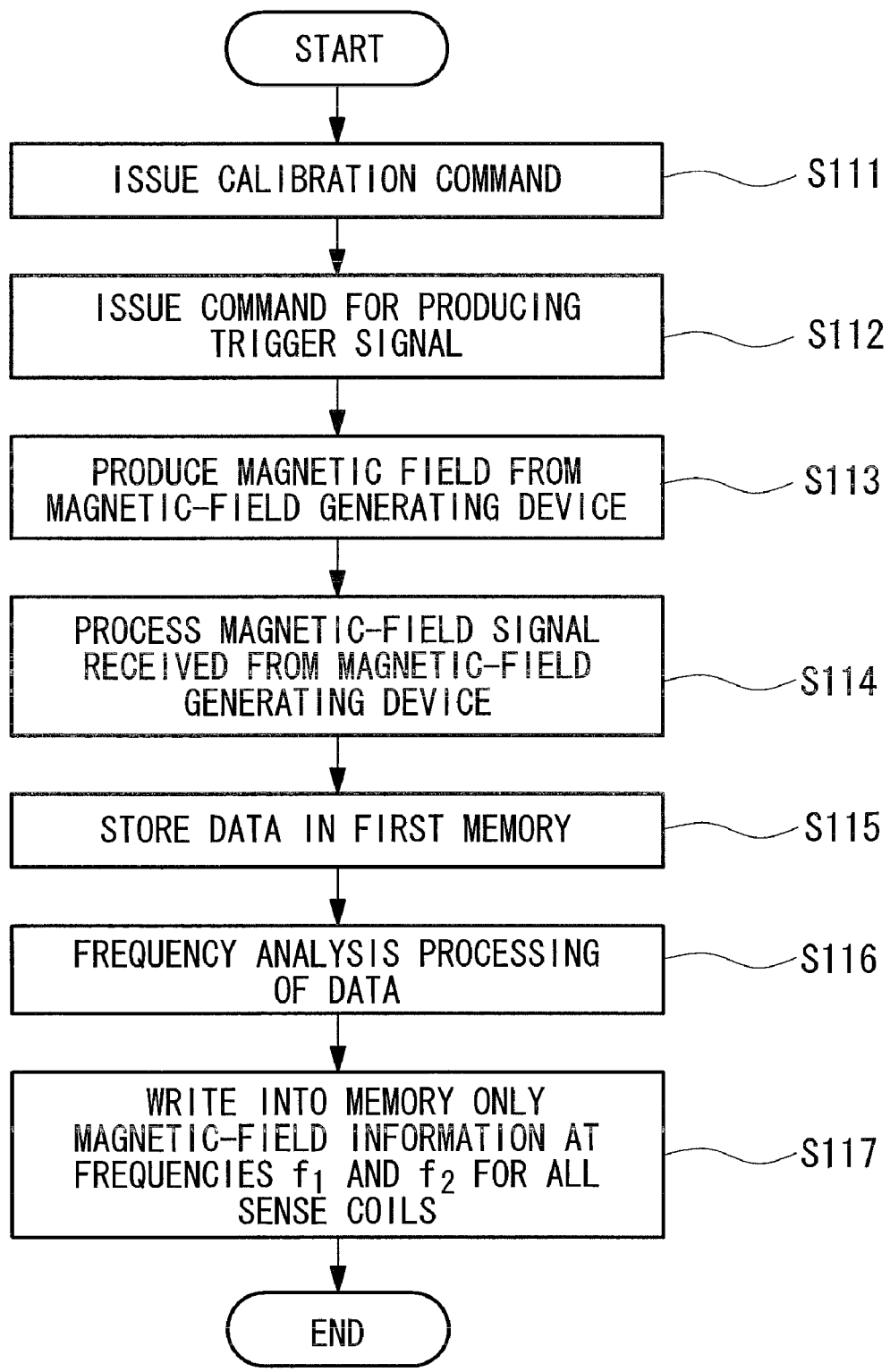
FIG. 21 is a flowchart illustrating calibration by the position detection method of FIG. 20.
Figure 22:
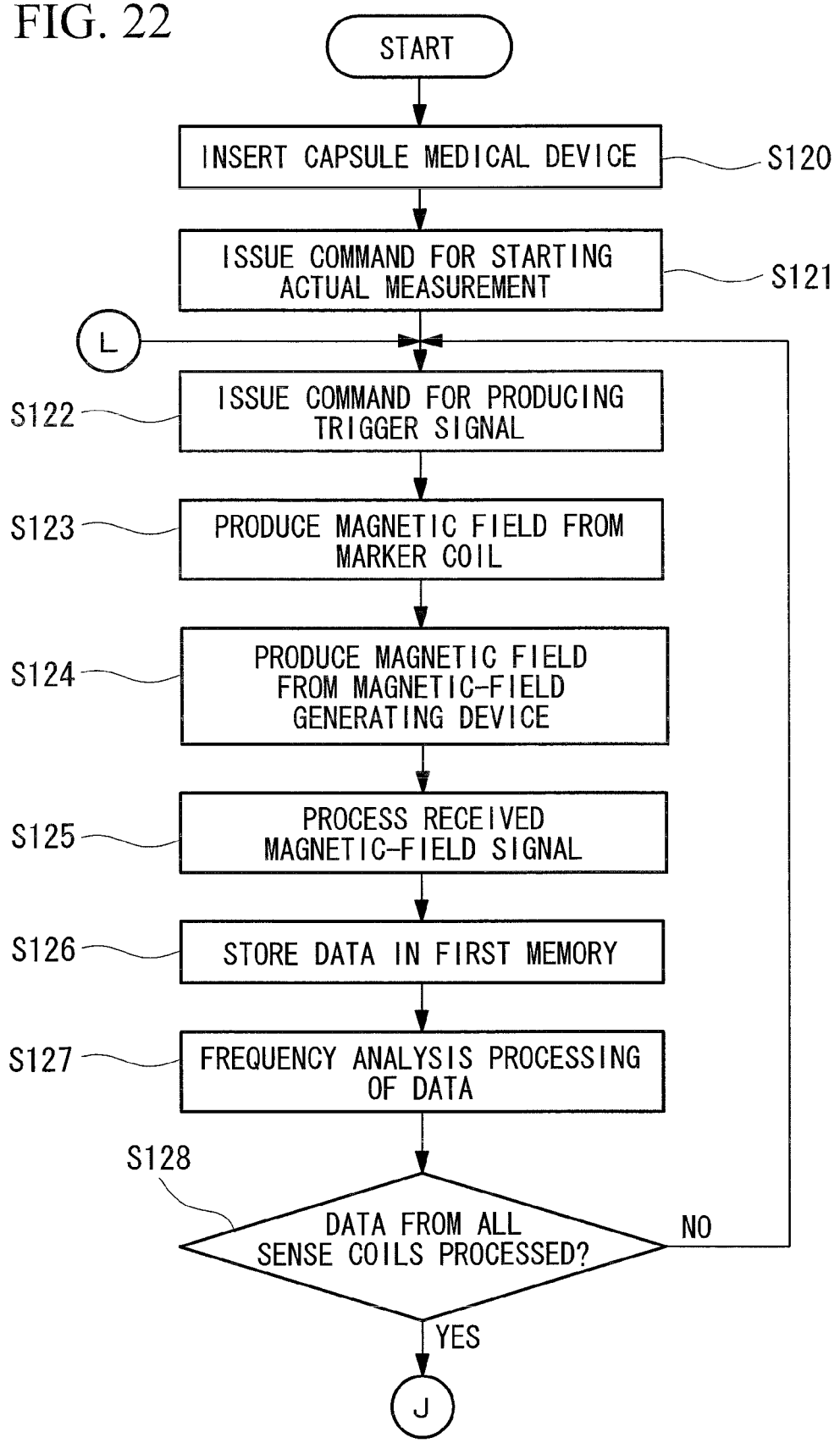
FIG. 22 is a flowchart illustrating the first-half stage of actual measurement by the position detection method using the position detection system shown in FIG. 18.

As shown in FIG. 19, the first capsule medical device 51 includes the marker coil 52 that produces the first alternating magnetic field having the first position-calculating frequency $f_0$, a marker-driving circuit 54 that drives the marker coil 52, a clock 55, a PLL circuit 56, a receiving section 57, and a power supply unit (not shown in the figure). The marker-driving circuit 54 produces the first alternating magnetic field in the marker coil 52 according to a command signal that is wirelessly transmitted from the transmission section 53 and is received by the receiving section 57.

The above-described magnetic-field generating device 41 produces the second alternating magnetic field having at least one set of second position-calculating frequencies $f_1$ and $f_2$ that are in the proximity of the resonance frequency (first position-calculating frequency $f_0$) of the magnetic induction coil 5 in the second capsule medical device 3' and that are separated from each other by substantially the same frequency with respect to that resonance frequency $f_0$ therebetween.

In order to detect the positions and the orientations of the marker coil 52 in the first capsule medical device 51 and the magnetic induction coil 5 in the second capsule medical device 3' by using the position detection system 50 according to this embodiment, waveform data of the produced alternating magnetic field is generated and stored in the waveform data memories 10 and 43, and then calibration is performed with the second capsule medical device 3' being disposed outside the working region.

The generated magnetic field waveform data is transferred to the waveform data memories 10 and 43 in the marker-driving circuit 54 of the first capsule medical device 51 and in the magnetic-field-generating-device driving circuit 42, respectively.

Generation of the magnetic-field waveform is started by inputting the resonance frequency $f_0$ of the magnetic induction coil 5 from the input device 26 (step S101). The control circuit 28 sets the input resonance frequency $f_0$ as the first position-calculating frequency $f_0$ of the first alternating magnetic field that is produced from the marker coil 52 in the first capsule medical device 51. Furthermore, the control circuit 28 sets the set of second position-calculating frequencies $f_1$ and $f_2$ that are separated from each other by substantially the same frequency with respect to the resonance frequency $f_0$ in between as frequencies of the second alternating magnetic field produced from the magnetic-field generating device 41 (step S102).

The control circuit 28 transfers the set frequencies $f_0$, $f_1$, and $f_2$ to the waveform-data generator 27 (step S103).

In the waveform-data generator 27, a magnetic-field waveform $B_G$ of the second alternating magnetic field produced from the magnetic-field generating device 41 is calculated by the expression below based on the sent second position-calculating frequencies $f_1$ and $f_2$ (step S104):

$$B_G = B_1 \times \sin(2\pi f_1 t) + B_2 \times \sin(2\pi f_2 t)$$

In addition, in the waveform-data generator 27, a magnetic-field waveform $B_{m1}$ of the first alternating magnetic field produced from the marker coil 52 is calculated by the expression below based on the sent first position-calculating frequency $f_0$:

$$B_{m1} = B_3 \times \sin(2\pi f_0 t)$$

Data for the magnetic-field waveform $B_{m1}$ generated in the waveform-data generator 27 is stored in the waveform data memory 43 of the magnetic-field-generating-device driving circuit 42. In addition, data for the magnetic-field waveform $B_G$ is transmitted from the transmission section 53 provided in the control section 7 to the receiving section 57 provided in the first capsule medical device 51. The magnetic-field waveform data received by the receiving section 57 is stored in the waveform data memory 10 (step S106).

Calibration is started by inputting a calibration command from the input device 26 while the first capsule medical device 51 is disposed in the body cavity and the second capsule medical device 3' is not disposed in the body cavity (step S111). The control circuit 28 instructs the trigger generator 31 to produce a trigger signal for the magnetic-field-generating-device driving circuit 42 and the read-out-timing generator 30. As a result, a trigger signal is issued from the trigger generator 31 (step S112).

The magnetic-field-generating-device driving circuit 42 that has received the trigger signal sequentially generates magnetic-field-generation driving signals in synchronization with the clock signal based on the data for the magnetic-field waveform $B_{m1}$ stored in the waveform data memory 43 and outputs them to the magnetic-field generating device 41. The magnetic-field generating device 41 produces the second alternating magnetic field based on the input magnetic-field-generation driving signals (step S113).

The receiving circuit 13b receives a magnetic-field signal associated with the second alternating magnetic field from the magnetic-field generating device 41 detected by each of the sense coils 13a; performs low-pass filtering, amplification, and band-pass filtering; and then performs A/D conversion in synchronization with the clock signal (step S114).

The magnetic-field signal that has been subjected to A/D conversion is stored in the first memory 19 of the position-calculating section 14 (step S115). Thereafter, it is determined whether or not a number of items of data required to perform frequency analysis processing are accumulated in the first memory 19, and if the required number of items of data are accumulated, frequency analysis processing is performed by the FFT-processing circuit 20 (step S116).

Based on the result of frequency analysis processing, the frequency-selecting section 24 extracts only the magnetic-field information at the second position-calculating frequencies $f_1$ and $f_2$, which are the frequencies of the second alternating magnetic field produced from the magnetic-field generating device 41, and stores it in the third memory 25 (step S117).

Let the intensities of the magnetic-field signals at the frequencies $f_1$ and $f_2$ stored here be $V_0^{f1-1}, V_0^{f1-2}, \ldots, V_0^{f1-N}$, $V_0^{f2-1}, V_0^{f2-2}, \ldots, V_0^{f2-N}$, where superscripts f1 and f2 represent frequency components, and the subsequent suffixes 1, 2, ... N represent the numbers of the sense coils 13a. The magnetic-field information in this case corresponds to information about the absolute value in the result of frequency analysis. Then, magnetic-field information of the frequencies $f_1$ and $f_2$ is stored in the third memory 25 as calibration values.

In this case, the magnetic-field signals at the frequency $f_1$ and the magnetic-field signals at the frequency $f_2$ detected by all the sense coils 13a may be corrected. More specifically, the sum $\Sigma(V_0^{f1-N})$ of the signal components at the frequency $f_1$ detected by all the sense coils 13a and the sum $\Sigma(V_0^{f2-N})$ of the signal components at the frequency $f_2$ detected by all the sense coils 13a are obtained. Then, $V_0^{f2-1}, V_0^{f2-2}, \ldots, V_0^{f2-N}$ are rewritten as follows and are overwritten in the first memory 19.

$V_0^{f2-1}$ is rewritten as $V_0^{f2-1} \times \Sigma(V_0^{f1-N})/\Sigma(V_0^{f2-N})$
$V_0^{f2-2}$ is rewritten as $V_0^{f2-2} \times \Sigma(V_0^{f1-N})/\Sigma(V_0^{f2-N})$
...
$V_0^{f2-N}$ is rewritten as $V_0^{f2-N} \times \Sigma(V_0^{f1-N})/\Sigma(V_0^{f2-N})$ In addition, $\Sigma(V_0^{f1-N})/\Sigma(V_0^{f2-N})$ is saved in the first memory 19. By doing so, $V_0^{f1-1}$ stored in the first memory 19 has a value substantially the same as the value of the replaced $V_0^{f2-1}$. In other words, the gain for the signal at the frequency $f_1$ of each of the sense coils 13a can be made substantially the same as the gain for the signal at the frequency $f_2$.

Furthermore, control is performed so that the clock (first clock) 55 provided in the first capsule medical device 51 is synchronized with the clock (second clock) 29 provided in the control section 7. More specifically, the synchronization signal of the second clock 29 and the trigger signal from the trigger generator 31 are transmitted from the transmission section 53 provided in the control section 7 to the receiving section 57 provided in the first capsule medical device 51. Then, the first clock 55 is phase-controlled by, for example, the PLL circuit 56 using the synchronization signal of the second clock 29. Such control is performed constantly or intermittently during calibration and actual measurement (described later).

Next, actual measurement is started when a command for starting actual measurement is entered on the input device 26 (step S121) with the first and second capsule medical devices 51 and 3' being disposed in the body cavity (step S120).

The control circuit 28 instructs the trigger generator 31 to produce a trigger signal for the marker-driving circuit 54, the magnetic-field-generating-device driving circuit 42, and the read-out-timing generator 30, and the trigger generator 31 produces a trigger signal (step S122).

Based on the waveform data stored in the waveform data memory 10, the marker-driving circuit 54 sequentially generates magnetic-field-generation driving signals in synchronization with the clock signal and outputs them to the marker coil 52. The marker coil 52 produces the first alternating magnetic field based on the input magnetic-field-generation driving signals (step S123).

In addition, based on the waveform data stored in the waveform data memory 43, the magnetic-field-generating-device driving circuit 42 sequentially generates magnetic-field-generation driving signals in synchronization with the clock signal and outputs them to the magnetic-field generating device 41. The magnetic-field generating device 41 produces the second alternating magnetic field based on the input magnetic-field-generation driving signals (step S124).

The receiving circuit 13b applies low-pass filtering, amplification, and band-pass filtering to magnetic-field signals associated with the first alternating magnetic field from the marker coil 52 and associated with the second alternating magnetic field from the magnetic-field generating device 41, i.e., the magnetic-field signals detected by each of the sense coils 13a, and then performs A/D conversion in synchronization with the clock signal (step S125).

The magnetic-field signals that have been subjected to A/D conversion are stored in the first memory 19 of the position-calculating section 14 (step S126). Then, it is determined whether or not a number of items of data required to perform frequency analysis processing are accumulated in the first memory 19, and if the required number of items of data are accumulated, frequency analysis processing is performed by the FFT-processing circuit 20 (step S127). Thereafter, it is determined whether or not the data from all the sense coils 13a have been subjected to this frequency analysis processing (step S128). If data from all sense coils 13a have not been processed, steps S122 to S127 are repeated.

Figure 23:
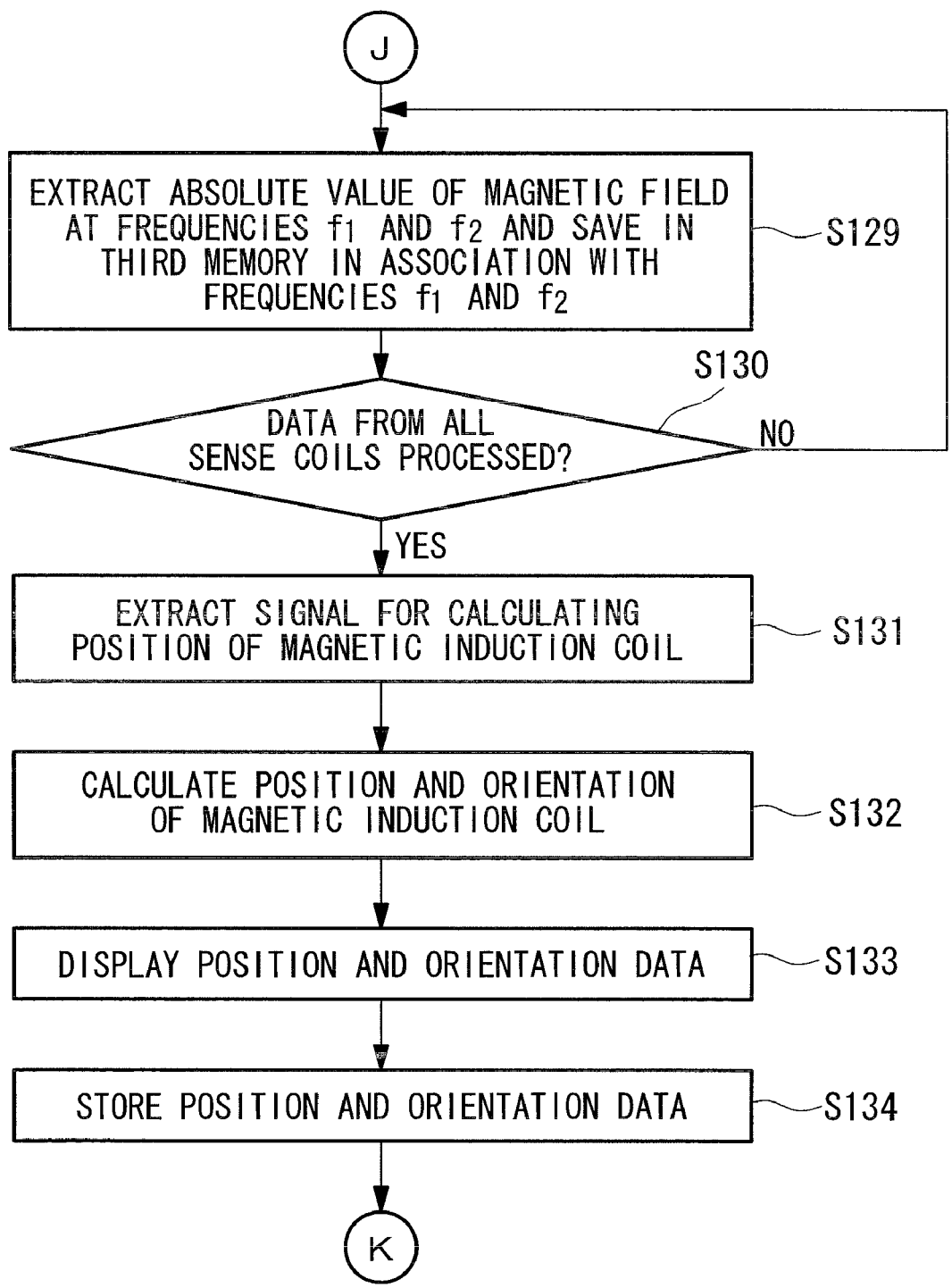
FIG. 23 is a flowchart illustrating actual measurement, continued from FIG. 22.
Figure 24:
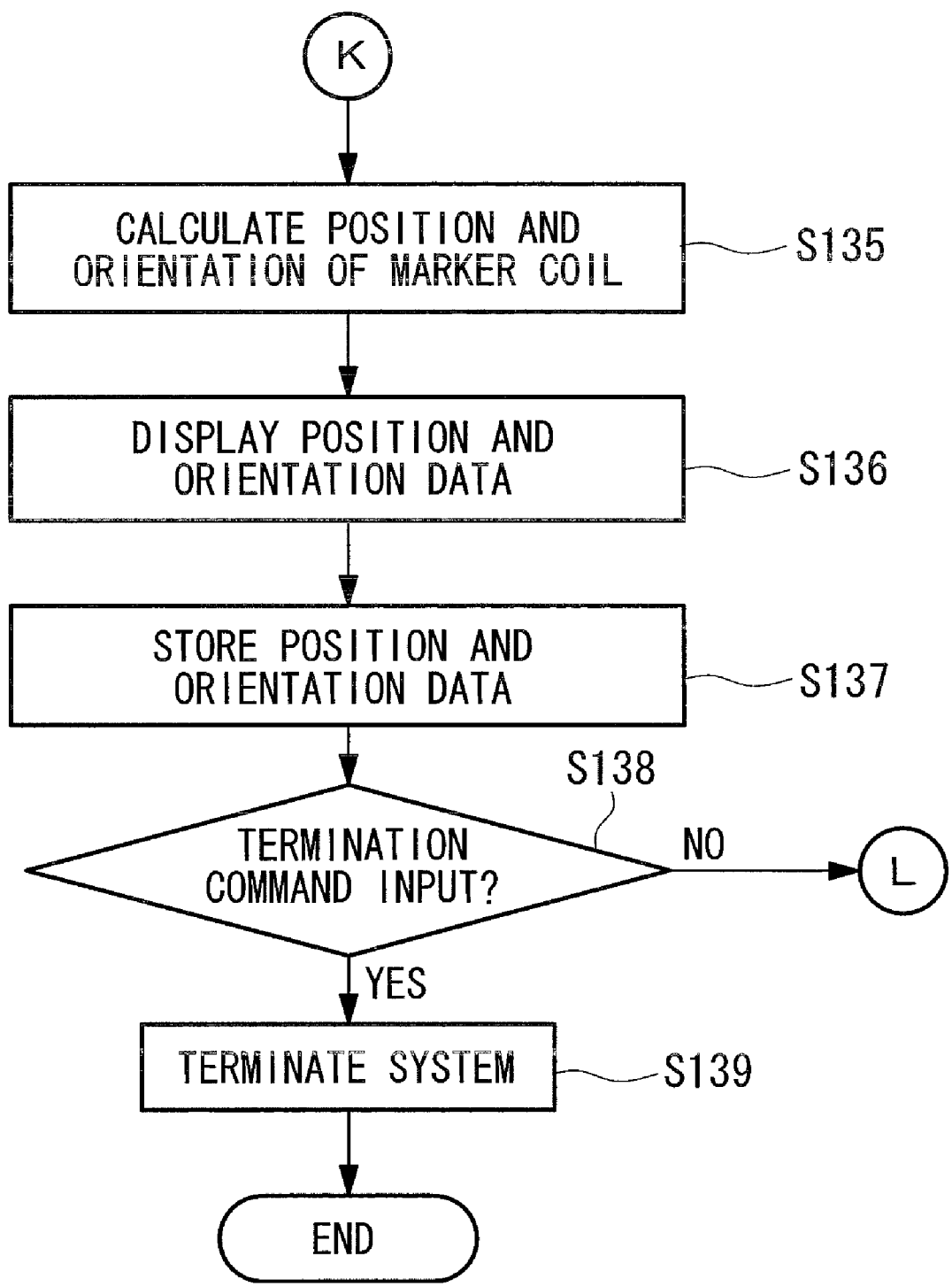
FIG. 24 is a flowchart illustrating actual measurement, continued from FIG. 23.

When the data from all the sense coils 13a have been subjected to frequency analysis processing, the frequency-selecting section 24 extracts, based on the result of processing, the absolute value of the magnetic-field intensity of the frequency components of the magnetic field produced by the magnetic-field-generating-device driving circuit 42, namely, the second position-calculating frequencies $f_1$ and $f_2$, as shown in FIG. 23; associates them with the frequencies $f_1$ and $f_2$; and stores them in the third memory 25 (step S129). This processing is applied to the magnetic-field signals from all the sense coils 13a (step S130).

The position/orientation analyzing section 22 uses the formulae below to calculate a signal of each of the sense coils 13a for performing position calculation of the magnetic induction coil 5 (step S131).

$$V_{m2}^1 = (V^{f1-1} - V_0^{f1-1}) - (V^{f2-1} - V_0^{f2-1})$$

$$V_{m2}^2 = (V^{f1-2} - V_0^{f1-2}) - (V^{f2-2} - V_0^{f2-2})$$

...

$$V_{m2}^N = (V^{f1-N} - V_0^{f1-N}) - (V^{f2-N} - V_0^{f2-N})$$

Then, based on the calculated $V_{m2}^1, V_{m2}^2, \ldots, V_{m2}^N$, the position/orientation analyzing section 22 calculates the position and the orientation of the magnetic induction coil 5 through repeated arithmetic operations (step S132).

The calculated position and the orientation of the magnetic induction coil 5 are sent to the control circuit 28, displayed on the display device 8 (step S133), and stored in the second memory 23 (step S134).

In addition, based on the result of frequency analysis processing, the frequency-selecting section 24 extracts the value of the real part of the magnetic-field intensity at the frequency component of the magnetic field produced by the marker-driving circuit 54, namely, the first position-calculating frequency $f_0$, and stores it in the third memory 25.

The position/orientation analyzing section 22 calculates the position and the orientation of the marker coil 52 based on the value of the real part of the magnetic-field intensity at the first position-calculating frequency $f_0$ stored in the third memory 25 (step S135).

The calculated position and the orientation of the marker coil 52 are sent to the control circuit 28, displayed on the display device 8 (step S136), and stored in the second memory 23 (step S137).

Then, it is checked whether or not a command for terminating position detection has been input on the input device 26 (step S138), and if a command for terminating position detection has been input, generation of a trigger signal from the trigger generator 31 is terminated to stop the operation of the position detection system 50 (step S139). On the other hand, if no termination command has been input, the flow returns to step S122, where the position detection operation is continued. In this case, for the initial values for repeated arithmetic operations of the positions and the orientations of the magnetic induction coil 5 and the marker coil 52, the calculation results of the positions and the orientations of the magnetic induction coil 5 and the marker coil 52 that have previously been calculated and stored in the second memory 23 are used. By doing so, the convergence time of repeated arithmetic operations can be reduced to calculate the positions and the orientations in a shorter period of time.

In this manner, according to the position detection system 50 and the position detection method of this embodiment, the signal from the marker coil 52 and the signal from the magnetic induction coil 5 can be completely separated from each other based on the phase information of both the signals. Therefore, the position and the orientation of the marker coil 52 can be calculated accurately. Furthermore, because the position and the orientation of the magnetic induction coil 5 are obtained based on the difference between two frequency-signal intensities, they can be calculated based on a signal in the case where no induced magnetic field from the marker coil 52 is present. As a result, the position and the orientation of the magnetic induction coil 5 can be obtained accurately by suppressing the interference caused by the marker coil 52.

In this embodiment, if a plurality of the marker coils 52 is provided, the plurality of marker coils 52 only need to be sequentially driven in a time-division manner to repeat steps S122 to S137.

The magnetic field produced by each marker coil 52 is a magnetic field having the frequency $f_0$, which is equal to the resonance frequency of the magnetic induction coil 5. For this reason, the induced magnetic field produced as a result of the magnetic induction coil 5 responding to the magnetic field from the marker coil 52 has a phase that is shifted by $\pi/2$ with respect to the phase of the magnetic field produced by the marker coil 52.

Therefore, the result of frequency analysis processing of signals acquired by the sense coils 13a reveals that the signals from the magnetic fields produced by the marker coil 52 and the magnetic induction coil 5 are shifted by $\pi/2$. The phase of the magnetic field produced by the marker coil 52 can be pre-adjusted because the sampling clock of the A/D converters 18 in the receiving circuit 13b is synchronized with the sampling clock of the D/A converter 11 in the marker-coil driving circuit 54. In this embodiment, adjustment is performed by the read-out-timing generator 30 so that any signal based on the magnetic field of the marker coil 52 is reflected in the real part.

For this adjustment method, only the marker coil 52 is driven to adjust the signal produced by the read-out-timing generator 30 so that the real part in the result of the frequency analysis processing applied to the magnetic-field signals acquired by the sense coils 13a exhibits the maximum value and the imaginary part in the same result exhibits the minimum value. This adjustment is needed only once, and re-adjustment is not required. This procedure can be achieved in the form of the calibration procedure described in the third embodiment in which the magnetic-field generating device 41 is replaced with the marker coil 52.

The invention claimed is:

1. A position detection system comprising:
a first marker placed in a first device insertable into a body lumen, configured to produce a first alternating magnetic field having a first position-calculating frequency by means of an external power supply;
a second marker placed in a second device insertable into a body lumen, the second device being different from the first device, the second marker including a magnetic induction coil having a resonance frequency equal to the first position-calculating frequency;
a magnetic-field detection section disposed outside a working region of the second marker and configured to detect a magnetic field at the first position-calculating frequency;
an extracting section that extracts, from the magnetic field detected by the magnetic-field detection section, a first detection-magnetic-field component having the first position-calculating frequency and having a phase equal to a phase of the first alternating magnetic field; and
a position/orientation analyzing section that calculates at least one of a position and an orientation of the first marker based on the intensity of the first detection-magnetic-field component extracted by the extracting section,
wherein the extracting section further extracts, from the magnetic field detected by the magnetic-field detection section, a second detection-magnetic-field component having the first position-calculating frequency and having a phase shifted by $\pi/2$ with respect to the phase of the first alternating magnetic field, and
the position/orientation analyzing section calculates at least one of a position and an orientation of the second marker based on the intensity of the second detection-magnetic-field component.

2. The position detection system according to claim 1, wherein
the extracting section further extracts, from the magnetic field detected by the magnetic-field detection section, a second detection-magnetic-field component having the first position-calculating frequency and having a phase shifted by $\pi/2$ with respect to the phase of the first alternating magnetic field, and
the position/orientation analyzing section calculates at least one of a position and an orientation of the second marker based on the intensity of the second detection-magnetic-field component.

3. The position detection system according to claim 2, comprising:
a magnetic-field generating unit, disposed outside a working region of the second marker, that produces a second alternating magnetic field having the first position-calculating frequency and having a phase equal to the phase of the first alternating magnetic field,
wherein the position/orientation analyzing section calculates at least one of the position and the orientation of the first marker based on a difference between an intensity of the first detection-magnetic-field component extracted when the first alternating magnetic field is produced and an intensity of the first detection-magnetic-field component extracted before the first alternating magnetic field is produced.

4. The position detection system according to claim 1, comprising:
a magnetic-field generating unit, disposed outside a working region of the second marker, that produces a second alternating magnetic field having at least one set of second position-calculating frequencies that are in the proximity of the first position-calculating frequency and are separated by a predetermined frequency with respect to the first position-calculating frequency with the first position-calculating frequency interposed therebetween,
wherein the magnetic-field detection section detects a magnetic field at the second position-calculating frequency,
the extracting section extracts, from the magnetic field detected by the magnetic-field detection section, a difference between intensities of at least one set of second detection-magnetic-field components having the one set of second position-calculating frequencies, and
the position/orientation analyzing section calculates at least one of a position and an orientation of the second marker based on the extracted difference.

5. The position detection system according to claim 4, wherein the intensities of the second detection-magnetic-field components are absolute-value intensities.

6. The position detection system according to claim 1, wherein the second marker is provided in a capsule medical device.

7. The position detection system according to claim 1, wherein the first marker is provided at a front end portion of an endoscope.

8. The position detection system according to claim 2, wherein the position detection system is included in a medical-device guidance system, and wherein the second marker further includes:
a magnetic-field acting section;
a propulsion-magnetic-field generating unit that produces a propulsion magnetic field made to act upon the magnetic-field acting section; and
a propulsion-magnetic-field control section that controls an intensity and a direction of the propulsion magnetic field based on at least one of the position and the orientation of the second marker calculated by the position/orientation analyzing section.

9. A position detection method comprising:
a magnetic-field generating step controlling a first marker placed in a first device insertable into a body lumen, to produce a first alternating magnetic field having a first position-calculating frequency by means of an external power supply;
an induced-magnetic-field generating step controlling a second marker placed in a second device insertable into a body lumen, the second device being different from the first device, the induced-magnetic field generating step including a magnetic induction coil to produce an induced magnetic field in response to the first alternating magnetic field;
a magnetic-field detecting step detecting a magnetic field at the first position-calculating frequency;
an extracting step extracting, from the detected magnetic field, a first detection-magnetic-field component having the first position-calculating frequency and having a phase equal to a phase of the first alternating magnetic field at the first position-calculating frequency; and a position/orientation analyzing step calculating at least one of a position and an orientation of the first marker based on the intensity of the extracted first detection-magnetic-field component,
wherein the extracting step includes extracting, from the detected magnetic field, a second detection-magnetic-field component having the first position-calculating frequency and having a phase shifted by $\pi/2$ with respect to the phase of the first alternating magnetic field, and
the position/orientation analyzing step includes calculating at least one of a position and an orientation of the second marker based on the intensity of the extracted second detection-magnetic-field component.

10. The position detection method according to 9, wherein:
the extracting step includes extracting, from the detected magnetic field, a second detection-magnetic-field component having the first position-calculating frequency and having a phase shifted by $\pi/2$ with respect to the phase of the first alternating magnetic field, and
the position/orientation analyzing step includes calculating at least one of a position and an orientation of the second marker based on the intensity of the extracted second detection-magnetic-field component.

11. The position detection method according to 9, wherein:
the magnetic-field generating step includes producing a second alternating magnetic field having the first position-calculating frequency and having a phase equal to the phase of the first alternating magnetic field,
the induced-magnetic-field generating step includes controlling the second marker to produce an induced magnetic field in response to the second alternating magnetic field, and
the position/orientation analyzing step includes calculating at least one of the position and the orientation of the first marker based on a difference between an intensity of the first detection-magnetic-field component extracted when the first alternating magnetic field is produced and an intensity of the first detection-magnetic-field component extracted before the first alternating magnetic field is produced.

12. The position detection method according to 9, wherein:
the magnetic-field generating step includes producing a second alternating magnetic field having at least one set of second position-calculating frequencies that are in the proximity of the first position-calculating frequency and are separated by a predetermined frequency with respect to the first position-calculating frequency with the first position-calculating frequency interposed therebetween,
the induced-magnetic-field generating step includes controlling the second marker to produce an induced magnetic field in response to the second alternating magnetic field,
the magnetic-field detecting step includes detecting a magnetic field at the second position-calculating frequency,
the extracting step includes extracting, from a detected magnetic field, a difference between intensities of at least one set of second detection-magnetic-field components having the one set of second position-calculating frequencies, and
the position/orientation analyzing step includes calculating at least one of a position and an orientation of the second marker based on the extracted difference.

* * * * *